(12) United States Patent
El Guindi et al.

(10) Patent No.: US 11,627,398 B2
(45) Date of Patent: Apr. 11, 2023

(54) HEARING DEVICE FOR IDENTIFYING A SEQUENCE OF MOVEMENT FEATURES, AND METHOD OF ITS OPERATION

(71) Applicant: Sonova AG, Stäfa (CH)

(72) Inventors: Nadim El Guindi, Zürich (CH); Anne Thielen, Stäfa (CH); Hans-Ueli Roeck, Hombrechtikon (CH); Julia Seiter, Stäfa (CH)

(73) Assignee: SONOVA AG, Stäfa (CH)

( * ) Notice: Subject to any disclaimer, the term of this patent is extended or adjusted under 35 U.S.C. 154(b) by 0 days.

(21) Appl. No.: 17/210,626

(22) Filed: Mar. 24, 2021

(65) Prior Publication Data

US 2021/0306726 A1 Sep. 30, 2021

(30) Foreign Application Priority Data

Mar. 24, 2020 (EP) .................................... 20165167

(51) Int. Cl.
*H04R 25/00* (2006.01)
*H04R 1/02* (2006.01)
*H04R 1/10* (2006.01)

(52) U.S. Cl.
CPC ........... *H04R 1/028* (2013.01); *H04R 1/1016* (2013.01); *H04R 1/1041* (2013.01); *H04R 25/30* (2013.01); *H04R 25/407* (2013.01); *H04R 25/65* (2013.01)

(58) Field of Classification Search
CPC .... H04R 1/028; H04R 1/1016; H04R 1/1041; H04R 25/30; H04R 25/407; H04R 25/65;
(Continued)

(56) References Cited

U.S. PATENT DOCUMENTS 10,959,028 B2 * 3/2021 Wurzbacher ......... H04R 25/505
2010/0256947 A1 10/2010 Kim et al.
(Continued)

OTHER PUBLICATIONS

European Search Report for European Patent Application No. 20165167.6 dated Aug. 21, 2020.
(Continued)

*Primary Examiner* — Phylesha Dabney
(74) *Attorney, Agent, or Firm* — Pearne & Gordon LLP

(57) ABSTRACT

Hearing device including a housing worn at a user's ear; a movement detector providing movement data indicating movement of the housing; and a processor identifying, based on the movement data, movement features in a sequence. The movement features represent movement activity by the user. The processor determines a temporal characteristic of the sequence of movement features and/or an amplitude characteristic of the movement data associated with a movement feature in the sequence. A method of operating the hearing device, and a computer-readable medium storing instructions to perform the method. The processor controls maintaining a data record representing the temporal characteristic and/or the amplitude characteristic determined at a plurality of times; determines a deviation measure indicating deviation between the data record and the temporal characteristic and/or the amplitude characteristic determined at a time later than the plurality of times; and controls operation of the hearing device depending on the deviation measure.

15 Claims, 10 Drawing Sheets

(58) Field of Classification Search
CPC .............. H04R 1/1091; H04R 2225/39; H04R 2225/41; H04R 2225/43; H04R 2225/55; H04R 2430/01; H04R 2460/13; H04R 25/505; H04R 25/554; H04R 3/005
USPC ........................................................ 381/328
See application file for complete search history.

(56) References Cited

U.S. PATENT DOCUMENTS

| | | |
|---|---|---|
| 2017/0323485 A1 | 11/2017 | Samec et al. |
| 2018/0133504 A1 | 5/2018 | Malchano et al. |
| 2018/0165922 A1 | 6/2018 | Hunt et al. |
| 2019/0231253 A1 | 8/2019 | Ahmed et al. |

OTHER PUBLICATIONS

Florentino-Liano, Blanca, et al: "Long term human activity recognition with automatic orientation estimation", Machine Learning for Signal Processing (MLSP), 2012 IEEE International Workshop On, IEEE, Sep. 23, 2012, pp. 1-6, XP032470885.

Welmer, A.-K., et al: "Walking Speed, Processing Speed, and Dementia: A Population-Based Longitudinal Study", Journals of Gerontology, Series A, Biological Sciences and Medical Sciences, Apr. 4, 2014, pp. 1503-1510, vol. 69, No. 12, XP055718786.

Mc Ardle, Ríona et al: "Do Alzheimer's and Lewy body disease have discrete pathological signatures of gait?", Alzheimer's & Dementia: The Journal of the Alzheimer's Associations, Elsevier, Sep. 20, 2019, pp. 1367-1377, vol. 15, No. 10, New York, NY, US, XP085862675.

\* cited by examiner

HEARING DEVICE FOR IDENTIFYING A SEQUENCE OF MOVEMENT FEATURES, AND METHOD OF ITS OPERATION

TECHNICAL FIELD

This disclosure relates to a hearing device comprising a movement sensor configured to provide movement data indicative of a movement of a housing of the hearing device, and a processor configured to identify, based on the movement data, a plurality of movement features in a sequence, the movement features representative of a movement activity carried out by the user, according to the preamble of claim 1. The disclosure also relates to a method of operating a hearing system, according to the preamble of claim 15, and a computer-readable medium storing instructions for performing the method.

BACKGROUND

Hearing devices are typically used to improve the hearing capability or communication capability of a user, for instance by compensating a hearing loss of a hearing-impaired user, in which case the hearing device is commonly referred to as a hearing instrument such as a hearing aid, or hearing prosthesis. The hearing device may pick up the surrounding sound with a microphone, process the microphone signal thereby taking into account the hearing preferences of the user of the hearing device, and provide the processed sound signal to an output transducer stimulating the user's hearing. The output transducer can be a miniature loudspeaker, commonly referred to as a receiver, for producing a sound in the user's ear canal. As another example, the output transducer can be an electrode array of a cochlear implant producing electric signals stimulating the auditory nerve. A hearing device may also be used to produce a sound in a user's ear canal based on an audio signal which may be communicated by a wire or wirelessly to the hearing device. Hearing devices are often employed in conjunction with communication devices, such as smartphones, for instance when listening to sound data processed by the communication device and/or during a phone conversation operated by the communication device. More recently, communication devices have been integrated with hearing devices such that the hearing devices at least partially comprise the functionality of those communication devices.

In recent years, some hearing devices have been equipped with a movement detector. The movement detector can be, for instance, an inertial sensor such as an accelerometer. The accelerometer data can be indicative of a movement of the hearing device and can thus be employed by a processor to identify a movement feature representative of a movement activity carried out by the user wearing the hearing device. For instance, the movement feature can be representative of a manual tapping on the housing carried out by the user, as disclosed in U.S. patent application numbers U.S. Ser. No. 16/367,328 and U.S. Ser. No. 16/368,880 and in European patent application number EP18195269.8. The movement feature can also be representative of a walking activity of the user, as disclosed in U.S. patent application number U.S. Ser. No. 16/370,777 and in European patent application number EP19166417.6. The movement feature can also be representative of a head rotation of the user, as disclosed in U.S. patent application number U.S. Ser. No. 16/370,536 and in European patent application number EP19183970.3. The movement feature can also be representative of a change of a pose of the user, for instance between a more upright pose and a more reclined pose, as disclosed in EP19166417.6. The movement feature can also be representative of a periodic movement of the user when listening to music content, as disclosed in European patent application number EP19217342.5.

The processor may control an operation of the hearing device depending on identifying the movement feature. The operation can comprise, for instance, changing a parameter of an acoustic beamforming or another sound processing program, as disclosed in U.S. Ser. No. 16/370,777 and EP19217342.5, or modifying a combination of an audio content provided by multiple audio sources such as an audio signal from a microphone and a streamed audio signal, as disclosed in U.S. Ser. No. 16/370,536, or changing a setting of the hearing device such as a volume control, as disclosed in U.S. Ser. No. 16/367,328, or evoking another operation such as accepting a phone call, as disclosed in EP18195269.8.

Some movement activities of the user can produce a sequence of the movement features identifiable by the processor. For instance, a walking activity involves a certain number of steps carried out by the user which each can produce a respective movement feature. Sequential manual tappings on the housing can produce a distinct movement feature at each tapping allowing to distinguish, for instance, a double tapping involving two manual tappings from a single tapping or a triple tapping. A rhythmical movement of the user can produce a sequence of movement features correlating with a music content presented to the user. Nodding or shaking the head, for instance during a conversation, can produce a corresponding sequence of movement features. Determining properties of the sequence of the movement features and/or intrinsic properties of the movement features within the sequence can allow to enhance a reliability of the detection of a specific movement activity based on the movement features and/or to differentiate between different kinds of movement activities carried out by the user.

The properties of the sequence and/or of the movement features within the sequence, however, may be influenced by various factors. Those factors can comprise a cognitive capability of the user, as well as a number and a difficulty of tasks performed by the user. For instance, when the user is involved in a communication with another individual during a walking activity, his walking behaviour can differ from a situation in which the cognitive capability of the user is purely focused on the walking. In such a situation, the user may unconsciously compensate the increased complexity of the dual task by decreasing the difficulty of one task, for instance by walking slower when listening and/or talking. The effect can be aggravated when the user is suffering from a cognitive decline, for example at an early onset of dementia, making it even more difficult to simultaneously comply with multiple tasks. Similarly, an autonomous movement task performed by the user can be influenced by those factors. For instance, a sequential manual tapping may be performed slower when the user's cognitive capability and/or attentiveness is decreased even though no other task may be performed at the same time. The properties of the sequence and/or the movement features within the sequence may thus change in different life situations and/or over time with increasing age. Consequently, the reliability of detecting a movement activity of the user and/or differentiating between movement activities based on those properties can be compromised. Operating the hearing device depending on the detected movement activity can thus be prone to error and lead to an unpleasant experience for the user.

SUMMARY

It is an object of the present disclosure to avoid at least one of the above mentioned disadvantages and to provide a hearing device and/or a method of operating the hearing device allowing to detect a movement activity carried out by the user in a more reliable way, in particular to allow for a reliability enhancement of a hearing device operation based on the detection. It is another object to collect information related to a hearing situation and/or a property of the user causing variations in the detection of the movement activity, wherein the information may be employed for an improved operation of the hearing device. It is a further object to assess a change of a cognitive capability of the user, in particular to obtain indications of a cognitive decline of the user, which can allow adapting an operation performed by the hearing device to such a cognitive change and/or to output information about such a cognitive change.

At least one of these objects can be achieved by a hearing device comprising the features of patent claim 1 and/or a method of operating a hearing device comprising the features of patent claim 15 and/or a computer-readable medium storing instructions for performing the method. Advantageous embodiments of the invention are defined by the dependent claims and the following description.

Accordingly, the present disclosure proposes a hearing device comprising a housing configured to be worn at an ear of a user, a movement detector mechanically coupled to the housing, wherein the movement detector is configured to provide movement data indicative of a movement of the housing, and a processor communicatively coupled to the movement detector. The processor is configured to identify, based on the movement data, a plurality of movement features in a sequence, the movement features representative of a movement activity carried out by the user; to determine a temporal characteristic of the sequence of movement features and/or to determine an amplitude characteristic of the movement data associated with at least one of the movement features identified in the sequence; to control maintaining of a data record representative of the temporal characteristic and/or the amplitude characteristic determined at a plurality of times; to determine a deviation measure indicative of a deviation between the data record and the temporal characteristic and/or the amplitude characteristic determined at a time later than said plurality of times; and to control an operation of the hearing device depending on the deviation measure.

Thus, by determining the deviation measure relative to said plurality of times temporally preceding said time later than said plurality of times, a detection of a movement activity carried out by the user can be realized in a more reliable way. This can be exploited for an enhanced reliability of controlling the operation following the movement activity detection. Determining the deviation measure can further allow to notice a hearing situation and/or a property of the user causing variations in the detection of the movement activity. For instance, the deviation measure can be used as an indicator of a change of a cognitive capability of the user.

Independently, the present disclosure proposes a method of operating a hearing device comprising a housing configured to be worn at an ear of a user. The method comprises providing movement data indicative of a movement of the housing; identifying, based on the movement data, a plurality of movement features in a sequence, the movement features representative of a movement activity carried out by the user; determining a temporal characteristic of the sequence of movement features and/or determining an amplitude characteristic of the movement data associated with at least one of the movement features identified in the sequence; maintaining a data record representative of the temporal characteristic and/or the amplitude characteristic determined at a plurality of times; determining a deviation measure indicative of a deviation between the data record and the temporal characteristic and/or the amplitude characteristic determined at a time later than said plurality of times; and controlling an operation of the hearing device depending on the deviation measure.

Independently, the present disclosure proposes a non-transitory computer-readable medium storing instructions that, when executed by a processor, cause a hearing device to perform operations of the method.

Subsequently, additional features of some implementations of the hearing device and/or the method of operating a hearing device are described. Each of those features can be provided solely or in combination with at least another feature. The features can be correspondingly provided in some implementations of the hearing device and/or of the method of operating the hearing device and/or the computer-readable medium.

In some implementations, the hearing device comprises a sound detector configured to provide sound data indicative of a detected sound, wherein the processor is communicatively coupled to the sound detector and configured to identify a sound feature from the sound data; and to associate the temporal characteristic and/or the amplitude characteristic with the sound feature depending on a temporal correlation between the sound feature and the sequence of movement features. By associating the temporal characteristic and/or the amplitude characteristic with the sound feature, the deviation measure can be determined in a more significant way for a specific movement activity carried out by the user. The data record may be representative of the temporal characteristic and/or the amplitude characteristic associated with the sound feature at said plurality of times. The deviation measure may be indicative of the deviation between the data record and the temporal characteristic and/or the amplitude characteristic associated with the sound feature at said time later than said plurality of times.

The sound detector may comprise a microphone and/or a voice activity detector (VAD). The processing unit may be configured to derive at least part of the sound data from the movement data provided by the movement detector. The sound feature can be representative of an own voice activity of the user. For instance, the sound feature may be representative of a speaking speed and/or a pronunciation accuracy and/or a stuttering and/or a number of speech pauses and/or a length of speech pauses. The sound feature can also be representative of an ambient sound in an environment of the user, in particular a sound generated by a sound source in an environment of the user.

In some instances, the movement features can be representative of a walking activity of the user. In some instances, the movement features can be representative of sequential manual tappings causing the movement of the housing.

In some implementations, the processor is configured to identify the movement activity carried out by the user based on determining whether the temporal characteristic and/or the amplitude characteristic corresponds to a predetermined parameter. For instance, the predetermined parameter can be indicative of a predetermined value of the temporal characteristic of the sequence of movement features and/or of the amplitude characteristic of the movement data associated with at least one of the movement features identified in the sequence. The operation can comprise adjusting the predetermined parameter depending on the deviation measure.

In some implementations, the operation comprises determining a parameter indicative of a listening intention of the user. In some implementations, the operation comprises determining a parameter indicative of an own voice activity of the user. In some implementations, the operation comprises determining a parameter indicative of a change of a cognitive capability of the user depending on the deviation measure. The parameter indicative of the change of a cognitive capability of the user may be determined to be indicative of a cognitive decline of the user when the deviation measure determined at said plurality of times is indicative of a temporal characteristic representative of a shorter time interval between the movement features as compared to the time interval determined at the time later than said plurality of times.

In some implementations, the operation comprises determining a parameter for a processing of sound data. In some instances, the hearing device comprises a microphone, in particular a microphone array, configured to detect ambient sound and a beamformer configured to form an acoustic beam based on the detected sound, wherein the operation comprises determining an optimized parameter for controlling a property of the acoustic beam. The property of the acoustic beam may be controlled depending on the deviation measure. Controlling the property of the acoustic beam may comprise reducing or increasing a directivity of the acoustic beam and/or changing a spatial direction of the acoustic beam.

In some instances, the hearing device comprises a microphone configured to provide first sound data based on detected ambient sound and a communication port configured to receive second sound data from a remote audio source, wherein the processor is configured to process the first sound data and second sound data in order to provide a combination of the first sound data and second sound data presented to the user, wherein the operation comprises changing the combination of the first sound data and second sound data. The combination may be changed depending on the deviation measure. In particular, the combination may be changed such that one of the first sound data and second sound data is more represented in a signal output by the output transducer and the other of the first sound data and second sound data is less represented in a signal output by the output transducer. For instance, the second sound data received from the remote device is a streamed audio signal.

In some implementations, the operation comprises providing a notification depending on the deviation measure. The notification may be based on a parameter determined depending on the deviation measure. For instance, the notification may be based on the parameter indicative of the change of a cognitive capability of the user and/or the parameter indicative of an own voice activity of the user and/or the parameter indicative of a listening intention of the user. In some instances, the notification may be output via a user interface of the hearing device. In some instances, the notification may be transmitted to a remote device via a communication link. In some instances, the notification may be stored in a memory of the hearing device.

In some implementations, the data record comprises a first data record representative of the temporal characteristic and/or the amplitude characteristic determined at a first plurality of times, wherein the processor is configured to control maintaining of a second data record, the second data record representative of the temporal characteristic and/or the amplitude characteristic determined at a second plurality of times, the first plurality of times temporally preceding the second plurality of times, wherein the deviation measure is indicative of a deviation between the first data record and the second data record. In some implementations, a deviation measure representative of a long term deviation of the temporal characteristic and/or the amplitude characteristic is determined between the first data record and the second data record. The long term deviation may indicate a deviation determined at a plurality of times within at least multiple days and/or weeks and/or months.

The data record may comprise a statistical measure of the temporal characteristic and/or the amplitude characteristic determined at said plurality of times. The statistical measure may comprise a mean value and/or a variance and/or a standard deviation of the temporal characteristic and/or the amplitude characteristic determined at said plurality of times, in particular at the first plurality of times and second plurality of times.

In some instances, the processor is configured to determine the temporal characteristic of the sequence of movement features, to control maintaining of the data record representative of the temporal characteristic and to determine the deviation measure such that the deviation measure is indicative of a deviation between the data record and the temporal characteristic. In some instances, the processor is configured to determine the amplitude characteristic of the movement data associated with at least one of the movement features identified in the sequence, to control maintaining of the data record representative of the amplitude characteristic and to determine the deviation measure such that the deviation measure is indicative of a deviation between the data record and the amplitude characteristic. In some instances, the processor is configured to determine the temporal characteristic of the sequence of movement features and the amplitude characteristic of the movement data, which amplitude characteristic is associated with at least one of the movement features identified in the sequence, to control maintaining of the data record representative of the temporal characteristic and the amplitude characteristic and to determine the deviation measure such that the deviation measure is indicative of a deviation between the data record and the temporal characteristic and the amplitude characteristic.

BRIEF DESCRIPTION OF THE DRAWINGS

Reference will now be made in detail to embodiments, examples of which are illustrated in the accompanying drawings. The drawings illustrate various embodiments and are a part of the specification. The illustrated embodiments are merely examples and do not limit the scope of the disclosure. Throughout the drawings, identical or similar reference numbers designate identical or similar elements. In the drawings.

DETAILED DESCRIPTION OF THE DRAWINGS

Figure 1:
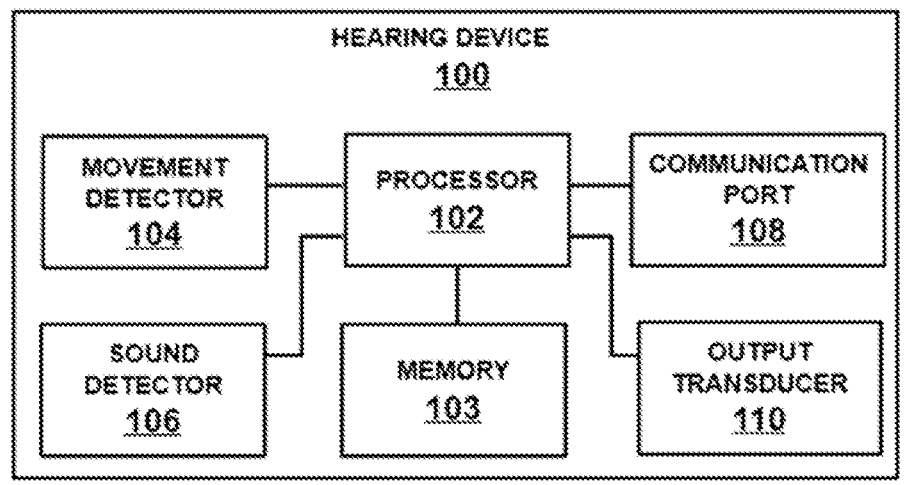
FIG. 1 schematically illustrates an exemplary hearing device including a processor, a movement detector, a sound detector, and an output transducer.

FIG. 1 illustrates an exemplary hearing device 100 configured to be worn at an ear of a user. Hearing device 100 may be implemented by any type of hearing device configured to enable or enhance hearing by a user wearing hearing device 100. For example, hearing device 100 may be implemented as a hearing instrument such as a hearing aid configured to detect sound and to provide an amplified version of the detected sound to a user, a cochlear implant system configured to provide electrical stimulation representative of the detected sound to a user, a bimodal hearing system configured to provide both amplification and electrical stimulation representative of the detected sound to a user, or any other suitable hearing prosthesis. In other examples, hearing device 100 may be implemented as an audio playing device, such as an earphone or headphone, configured to produce a sound to a user based on an audio signal which may be communicated by a wire or wirelessly to the hearing device. Hearing device 100 may also be implemented as a hearing instrument configured to operate as an audio playing device in an accessory functionality.

Different types of hearing device 100 can also be distinguished by the position at which they are intended to be worn at the ear level of the user. Some types of hearing devices comprise a behind-the-ear part (BTE part) including a housing configured to be worn at a wearing position behind the ear of the user, which can accommodate functional components of the hearing device. Hearing devices with a BTE part can comprise, for instance, receiver-in-the-canal (RIC) hearing aids and behind-the-ear (BTE) hearing aids. Other functional components of such a hearing device may be intended to be worn at a different position at the ear, in particular at least partially inside an ear canal. For instance, a RIC hearing aid may comprise a receiver intended to be worn at least partially inside the ear canal. The receiver may be implemented in a separate housing, for instance an earpiece adapted for an insertion and/or a partial insertion into the ear canal. A BTE hearing aid may further comprise a sound conduit, for instance a sound tube, intended to be worn at least partially inside the ear canal. Other types of hearing devices, for instance earbuds, earphones, and hearing instruments such as in-the-ear (ITE) hearing aids, invisible-in-the-canal (IIC) hearing aids, and completely-in-the-canal (CIC) hearing aids, commonly comprise a housing intended to be worn at a position at the ear such that they are at least partially inserted inside the ear canal. An additional housing for wearing at the different ear position may be omitted in those devices.

In the illustrated example, hearing device 100 includes a processor 102 communicatively coupled to a movement detector 104, a sound detector 106, a memory 103, a communication port 108, and an output transducer 110. Output transducer 110 may be implemented by any suitable audio output device, for instance a loudspeaker or a receiver of a hearing aid or an output electrode of a cochlear implant system.

Movement detector 104 may be implemented by any suitable detector configured to provide movement data indicative of a movement of a user. In particular, movement detector 104 may comprise at least one inertial sensor. The inertial sensor can include, for instance, an accelerometer configured to provide the movement data representative of an acceleration and/or displacement and/or rotation, and/or a gyroscope configured to provide the movement data representative of a rotation. Movement detector 104 may also comprise an optical detector such as a camera. The movement data may be provided by generating optical detection data over time and evaluating variations of the optical detection data. Movement detector 104 may also comprise an electronic compass such as a magnetometer. Movement detector 104 can be configured to provide the movement data over time in subsequent periods. Movement detector 104 can be mechanically coupled to a housing of hearing device 100 such that it remains in a fixed position relative to the housing upon a translational and/or rotational displacement of the housing. Thus, the movement data provided by movement detector 104 is indicative of a movement of the housing and a corresponding movement of the user wearing the housing at an ear.

Sound detector 106 may be implemented by any suitable sound detection device, such as a microphone, in particular a microphone array, and/or a voice activity detector (VAD), and is configured to detect a sound presented to a user of hearing device 100. The sound can comprise ambient sound such as audio content (e.g., music, speech, noise, etc.) generated by one or more sound sources in an ambient environment of the user. The sound can also include audio content generated by a voice of the user during an own voice activity, such as a speech by the user. The own voice activity may be detected by a VAD. The VAD may be configured to detect sound from bone conducted vibrations transmitted from the user's vocal chords to the user's ear canal and/or to estimate an own voice sound portion from sound detected by an ambient microphone and/or an ear canal microphone. In some implementations, sound detector 106 includes movement detector 104. In particular, the movement data provided by movement detector 104 can be indicative of an own voice activity of the user. For instance, an accelerometer may be employed as a movement detector to provide movement data indicative of a movement of the user and as a VAD to detect an own voice activity of the user, as described in European patent application No. EP19166291.5. Sound detector 106 is configured to output sound data indicative of the detected sound. Sound detector 106 may be included in or communicatively coupled to hearing device 100 in any suitable manner.

Memory 103 may be implemented by any suitable type of storage medium and is configured to maintain, e.g. store, data controlled by processor 102, in particular data generated, accessed, modified and/or otherwise used by processor 102. For example, processor 102 may control memory 103 to maintain a data record based on data generated by a processing of the movement data provided by movement detector 104 and/or the sound data provided by sound detector 106. Memory 103 may also be configured to store instructions for operating hearing device 100 that can be executed by processor 100, in particular an algorithm and/or a software that can be accessed and executed by processor 102.

Communication port 108 may be implemented by any data transmitter or data receiver or data transducer configured to exchange data with a remote device via a communication link. For instance, the remote device may be a handheld device such as a smartphone and/or a stationary processing unit such as a personal computer (PC). Communication port 108 may be configured for wireless data communication. For instance, data may be communicated in accordance with a Bluetooth™ protocol and/or by any other type of radio frequency communication such as, for example, data communication via an internet connection and/or a mobile phone connection. The transmitted data may comprise data maintained in a memory of the remote device, which may be controlled by processor 102. In particular, processor 102 may be configured to control maintaining of the data record in the memory of the remote device based on data generated by a processing of the movement data and/or the sound data in addition to or in place of memory 103.

Processor 102 is configured to access the movement data provided by movement detector 104 and to access the sound data provided by sound detector 104. Processor 102 is further configured to control maintaining of a data record based on properties determined from the movement data and/or the sound data. These and other operations that may be performed by processor 102 are described in more detail in the description that follows.

A temporal characteristic of the sequence of movement features, as used herein, may be any parameter characteristic for the temporal sequence of the movement features. In particular, the temporal characteristic may be indicative of a time interval between at least two movement features in the sequence. In some instances, the temporal characteristic may be provided as a time interval by which the movement features are separated in the sequence. In some instances, the temporal characteristic may be provided as a frequency in which the movement features occur in the sequence. In some instances, the temporal characteristic may be provided as a number of the movement features within a sequence of a known duration. The temporal characteristic may comprise multiple values each indicative of the time interval between two consecutive movement features in the sequence and/or a value representative of the time interval between multiple consecutive movement features. For instance, the temporal characteristic may comprise a mean value of the time interval between multiple consecutive movement features.

An amplitude characteristic of the movement data associated with at least one of the movement features identified in the sequence, as used herein, may be any parameter characteristic for an amplitude of the movement data, which is associated with at least one of the movement features identified in the sequence. In some instances, the amplitude characteristic may be characteristic for an amplitude of the movement data associated with at least two of the movement features identified in the sequence. The amplitude characteristic may correspond to an amplitude of a segment of the movement data from which the at least one movement feature has been identified and/or may correspond to the at least one movement feature identified in the sequence. The amplitude characteristic may also be derived from a segment of the movement data from which the at least one movement feature has been extracted and/or may be derived from the amplitude corresponding to the at least one movement feature identified in the sequence.

Movement data based on which at least one of the movement features has been identified in the sequence may be associated with the identified movement feature. In some instances, movement data used as a basis for identifying at least two consecutive movement features in the sequence and/or all movement features in the sequence may be employed to determine the amplitude characteristic. In some instances, multiple amplitude characteristics may be determined from movement data associated with multiple movement features identified in the sequence. In some instances, the amplitude characteristic may be representative of movement data associated with multiple movement features identified in the sequence. For instance, the amplitude characteristic may be determined as a mean value of multiple amplitudes each determined from movement data associated with a respective movement feature identified in the sequence.

A deviation measure, as used herein, may be any parameter indicative of the deviation between the data record and the temporal characteristic and/or the amplitude characteristic determined at the different time. For instance, the deviation measure may be determined as a difference between the respective values. A size of the difference may indicate a magnitude of the deviation. The deviation measure may also comprise a statistical measure. The statistical measure may be determined between the data record and the temporal characteristic and/or the amplitude characteristic determined at the different time, wherein at least one of the data record and the temporal characteristic and/or the amplitude characteristic determined at the different time may comprise multiple values on which the statistics may be based. In particular, an average absolute deviation and/or a least absolute deviation may be employed as the deviation measure.

Controlling the maintaining of the data record may comprise collecting data based on the temporal characteristic and/or the amplitude characteristic determined at the plurality of times. The plurality of times may be distributed over a prolonged period of time such as, for instance, at least multiple days and/or weeks and/or months. Controlling the maintaining of the data record may further comprise storing and/or accessing and/or modifying data based on the temporal characteristic and/or the amplitude characteristic determined at the plurality of times in a memory. In some instances, the memory is included in the hearing device. In some other instances, the memory is included in a remote device operable at a position remote from the ear at which the hearing device is worn and communicatively coupled to the hearing device. For instance, the remote device may be a handheld device such as smart phone or a stationary device such as a personal computer. Controlling the maintaining of the data record may further comprise updating the data stored in the memory based on the temporal characteristic and/or the amplitude characteristic determined at the time later than the plurality of times. In particular, controlling the maintaining of the data record may comprise data logging based on the temporal characteristic and/or the amplitude characteristic determined at the plurality of times.

Figure 2:
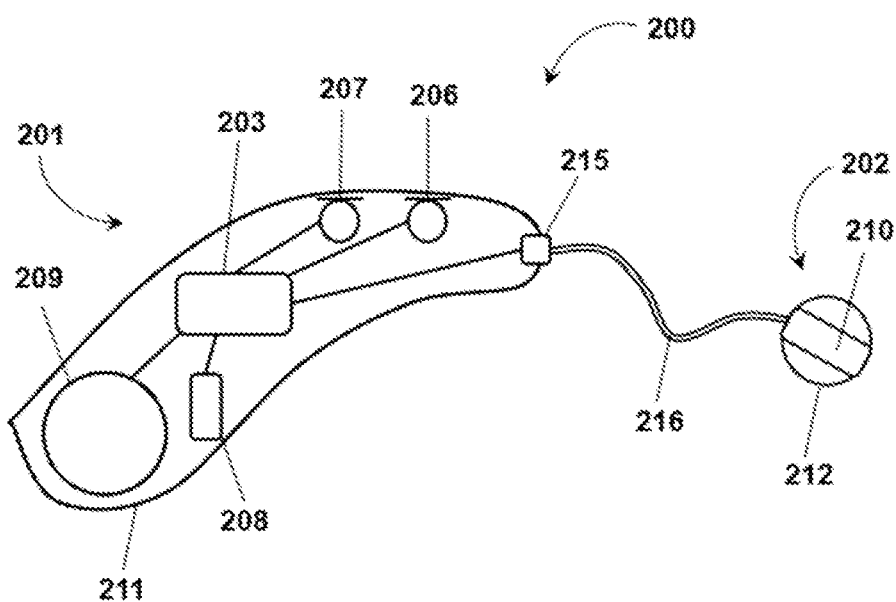
FIG. 2 schematically illustrates some embodiments of an exemplary hearing device in the form of a RIC hearing aid.

FIG. 2 illustrates exemplary implementations of hearing device 100 as a RIC hearing aid 200, in accordance with some embodiments of the present disclosure. RIC hearing aid 200 comprises a BTE part 201 configured to be worn at an ear at a wearing position behind the ear. Hearing aid 200 further comprises an ITE part 202 configured to be worn at the ear at a wearing position at least partially inside an ear canal of the ear. Hearing aid 200 comprises a first housing 211 of BTE part 201 and a second housing 212 of ITE part 202. First housing 211 accommodates a processing unit 203. Processing unit 203 includes processor 102. Processing unit 203 may further include memory 103 and/or communication port 108. Processing unit 203 may further comprise an amplifier.

First housing 211 also accommodates sound detector 106 and movement detector 108. In the example, sound detector 106 is provided by a plurality of spatially arranged microphones 206, 207. Microphones 206, 207 can be included in a microphone array. Microphones 206, 207 are configured to provide sound data to processing unit 203. The sound data can be indicative of an ambient sound and/or an own voice activity of the user. In the example, movement detector 108 is an accelerometer 208 configured to provide movement data indicative of a movement of first housing 211. Furthermore, a battery 209 is enclosed by first housing 211.

Output transducer 110 is provided as a receiver 210 accommodated in second housing 212 of ITE part 202. BTE part 201 and ITE part 202 are interconnected by a cable 216. Receiver 210 is communicatively coupled to processing unit 203 via cable 216 and a cable connector 215 provided at first housing 211 of BTE part 201. A wireless coupling between processing unit 203 and receiver 110 is also conceivable. In some other implementations, movement detector 108 and/or sound detector 106 can be accommodated in second housing 212 of ITE part 202.

Figure 3:
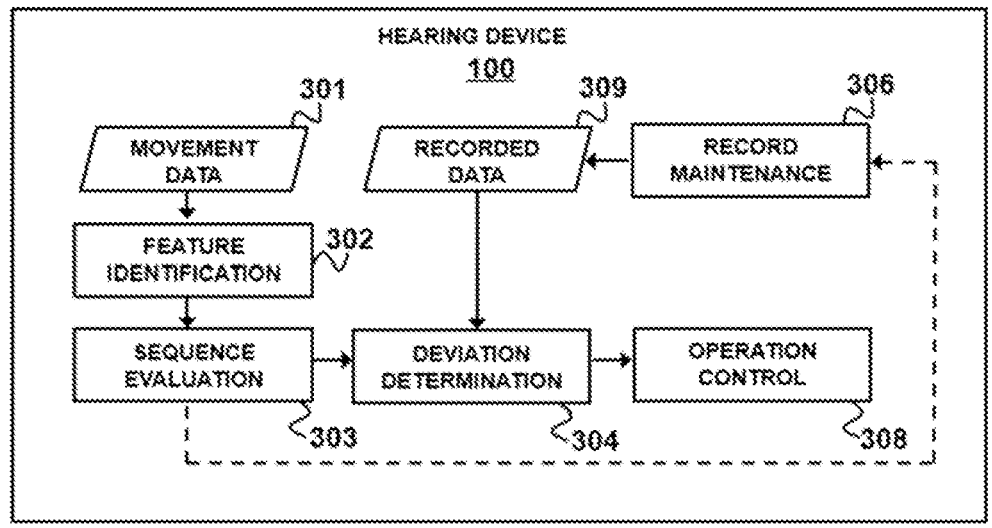
FIGS. 3-5 schematically illustrate exemplary configurations of a hearing device to identify, based on movement data, a plurality of movement features in a sequence, and to determine a deviation measure of the sequence with respect to recorded data.

FIG. 3 illustrates a functional block diagram of an exemplary movement data processing algorithm that may be executed by processor 102. As shown, the algorithm is configured to be applied to movement data 301 provided by movement detector 104. The movement data is input to processor 102. The algorithm comprises modules 302-308.

A feature identification module 302 can identify, based on movement data 301, a plurality of movement features in a temporal sequence, wherein the movement features are representative of a movement activity carried out by the user. A sequence evaluation module 303 can determine a property of the sequence of movement features. To illustrate, the movement features may be produced in the movement data, for instance, by a physical activity of the user involving periodic movements which may result in a sequence of movement features with related properties. The related properties can be employed by feature identification module 302 to identify the movement features in the sequence. Moreover, after or during the feature identification performed by module 302, a property of the sequence can be determined by sequence evaluation module 303. To this end, feature identification module 302 and sequence evaluation module 303 may be operatively combined to a single module in order to simultaneously identify the movement features and determine the property of the sequence, or in two separate modules to first identify the movement features and then determine the property of the sequence.

A record maintenance module 306 can control maintaining of a data record 309 representative of the property of the sequence of movement features determined at a plurality of times by sequence evaluation module 303, as indicated by a dashed arrow. Data record 309 may be maintained in memory 103 and/or in a memory of a remote device, wherein the data may be transmitted to the remote device via communication port 108. Data record 309 may be also be maintained in a remote memory, such as a cloud, wherein the data may be transmitted to the remote memory via communication port 108. In particular, data record 309 may be maintained based on the property of the sequence of movement features determined over a long term, for instance a plurality of times per day during the course of several days or weeks or months or years. Thus, data record 309 can be representative of a long term character of the property of the sequence of movement features determined at the plurality of times. Statistical outliers may be identified and/or averaged with recurring values.

A deviation determination module 304 can determine a deviation measure indicative of a deviation between data record 309 and the property of the sequence of movement features determined at a time later than said plurality of times. The plurality of times for which data record 309 is representative can thus be temporally preceding said later time. For instance, the later time may be a current time. The deviation measure may thus be representative of a momentary change of the property of the sequence of movement features with respect to earlier times. Processor 102 may be configured to access data record 309 from memory 103 and/or from the memory of the remote device via communication port 108. Processor 102 may be further configured to compare data record 309 with the property of the sequence of movement features determined at the later time by sequence evaluation module 303 in order to determine the deviation measure.

For instance, the deviation measure may comprise a difference between a value of data record 309 and the property of the sequence of movement features determined at the later time. The deviation measure may also comprise a statistical measure. In some instances, the statistical measure may be based on determining the deviation measure between a first data record and a second data record each maintained by record maintenance module 306. The first data record and the second data record may be representative of the property of the sequence of movement features determined by sequence evaluation module 303 at a different plurality of times. For instance, a first plurality of times on which the first data record is based may be temporally preceding a second plurality of times on which the second data record is based. This may comprise maintaining the first data record and the second data record based on the property of the sequence of movement features periodically determined over a long term. The term may be different for the first data record and the second data record. Thus, each of the first data record and the second data record may comprise statistically representative values based on the property of the sequence of movement features determined at the respective plurality of times. The deviation measure may then comprise, for instance, a difference between a statistical mean of the property of the sequence of movement features determined at the respective plurality of times. The deviation measure may also account for a variance and/or a standard deviation from the respective statistical mean.

An operation control module 308 can control an operation of the hearing device depending on the deviation measure. For instance, processor 102 may be configured to control the operation when the deviation measure exceeds a threshold. The threshold may be predetermined. The threshold may also be determined by processor 102 depending on data record 309, for instance as a function of a statistical measure of the data record such as a variance or standard deviation.

Controlling the operation by operation control module 308 may comprise invoking and/or improving another operation or functionality of the hearing device. In some implementations, the operation comprises determining a parameter for identifying a movement activity carried out by the user. For example, the parameter may be based on the deviation measure determined by deviation determination module 304. In some implementations, the operation comprises determining an optimized parameter for performing another operation of the hearing device. In some instances, the other operation may be related to a digital signal processing (DSP) of sound data. For example, the sound data may comprise the sound data provided by sound detector 106. The operation can comprise, for instance, adjusting a property of an acoustic beam provided by a beamforming which may be performed by processor 102. More particularly, the operation may comprise reducing or increasing a directivity of the acoustic beam and/or changing a spatial direction of the acoustic beam. The sound data may also comprise data communicated by a wire or wirelessly to the hearing device, for instance a streamed audio signal. The operation may comprise modifying a combination of an audio content presented to the user, wherein the combined audio content may be based in part on the sound data provided by the sound detector and in part on the sound data communicated to the hearing device. The operation may also comprise changing a setting of the hearing device, for instance a volume control.

In some implementations, the operation comprises determining a parameter indicative of a property of the user, which may include a change of the user property over time. For instance, the user property may be a communication behavior, such as an own voice activity, or a user intention, such as a listening intention. The user property may also be a cognitive capability of the user. The parameter may then be indicative of a change of the cognitive capability such as, for instance, a cognitive decline. The operation may further comprise providing a notification based on the determined parameter. The notification may be output to the user by a user interface. The notification may also be stored in memory 103 and/or transmitted to a remote device via communication port 108 such that it can be retrieved at a later time, for instance by the user and/or a health care professional (HCP) and/or a medical doctor and/or a significant other of the user.

Figure 4:
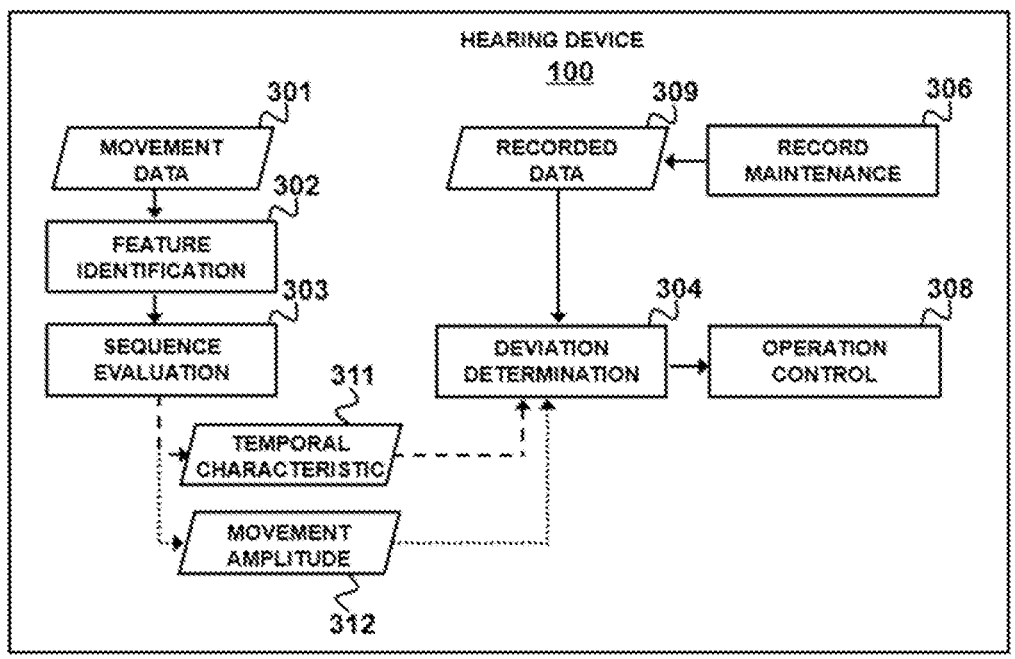

FIG. 4 illustrates a functional block diagram of an algorithm, which may be implemented in accordance with some implementations of the algorithm illustrated in FIG. 3. As shown, the property of the sequence of movement features determined by sequence evaluation module 303 can comprise a temporal characteristic 311 of the sequence of movement features and/or an amplitude characteristic 312 of the movement data associated with at least one of the movement features identified in the sequence. To illustrate, temporal characteristic 311 may be indicative of a time interval between at least two movement features identified in the sequence. Amplitude characteristic 312 may be an amplitude of the movement data employed by feature identification module 302 to identify the respective movement feature and/or an amplitude of the movement data not employed by feature identification module 302 but which may be characteristic for the sequence of movement features.

In some implementations, the property of the sequence of movement features determined by sequence evaluation module 303 includes temporal characteristic 311 without amplitude characteristic 312. In some implementations, the determined property of the sequence of movement features includes amplitude characteristic 312 without temporal characteristic 311. In some implementations, the determined property of the sequence of movement features includes both temporal characteristic 311 and amplitude characteristic 312. In some instances, temporal characteristic 311 and amplitude characteristic 312 of consecutive movement features within the sequence may be correlated. The property of the sequence of movement features determined by sequence evaluation module 303 can thus be employed as an identifier for the sequence relative to a certain time. The determined property can thus be used, on the one hand, to identify a corresponding sequence of movement features at a later time and/or, on the other hand, to determine a deviation of the property of another sequence determined at a later time.

Temporal characteristic 311 and/or amplitude characteristic 312 may be input from sequence evaluation module 303 to record maintenance module 306, as indicated by the dashed arrow in FIG. 3. Data record 309 may thus be based on temporal characteristic 311 and/or amplitude characteristic 312 determined at a plurality of times by sequence evaluation module 303.

Figure 5:
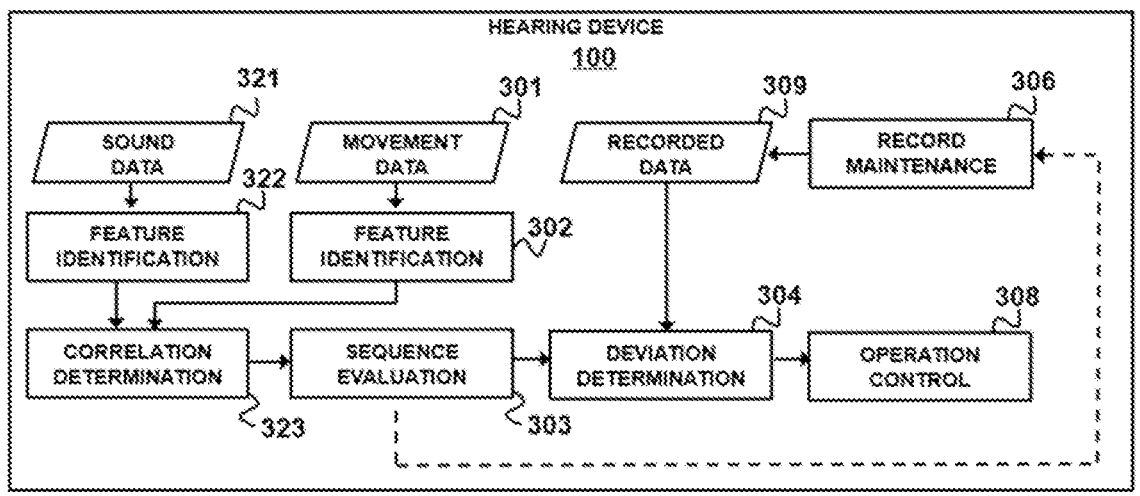

FIG. 5 illustrates a functional block diagram of an exemplary movement data and sound data processing algorithm that may be executed by processor 102. As shown, the algorithm is configured to be applied to movement data 301 provided by movement detector 104 and to sound data 321 provided by sound detector 106. The movement data and sound data is input to processor 102. The algorithm comprises modules 302-308 described above.

A feature identification module 322 can identify, based on sound data 321, at least one sound feature. The sound data may include ambient sound data detected in an environment of the user and/or ear canal sound data detected inside an ear canal of the user and/or own voice sound data detected by a VAD. Own voice characteristics of the user may be included in the own voice sound data and/or in the ambient sound data and/or in the ear canal sound data. In some instances, the sound feature identified by sound identification module 322 can be indicative of an own voice activity of the user. In some instances, the sound feature identified by sound identification module 322 can be indicative of an ambient sound in the environment of the user, for instance a sound generated by a sound source in the environment such as a conversation partner of the user.

A correlation determination module 323 can determine a temporal correlation between the sequence of movement features identified by movement feature identification module 302 and the sound feature identified by sound identification module 322. Sequence evaluation module 303 can then determine the property of the sequence of movement features, which can include temporal characteristic 311 and/or amplitude characteristic 312, depending on a degree of correlation between the sequence of movement features and the sound feature exceeding a threshold. Thus, depending on the correlation, the property of the sequence of movement features determined by sequence evaluation module 303 can be associated with the sound feature. As a result, data record 309 maintained by record maintenance module 306 can be based on the property of the sequence of movement features associated with the sound feature. Moreover, the deviation measure determined by deviation determination module 304 can be indicative of the deviation between the data record and the property of the sequence of movement features associated with the sound feature.

To illustrate, a movement activity of a certain type carried out by the user may change in a situation in which the sound feature can be identified in the sound data as compared to a situation in which the sound feature is absent. Correspondingly, a temporal coincidence between the sound feature and the sequence of movement features may be employed as an indication for a situation in which the sequence of movement features has a property determined by sequence evaluation module 303 which is specific for the sound feature. By associating the property of the sequence of movement features with the sound feature in the above described way, the determined property can then be employed, on the one hand, to identify a corresponding sequence of movement features associated with a corresponding sound feature at a later time and/or, on the other hand, to determine a deviation of the property of another sequence determined at a later time depending on whether a corresponding sound feature is also determined at the later time. In this way, a detection reliability of the movement activity carried out by the user can be enhanced.

Figure 6:
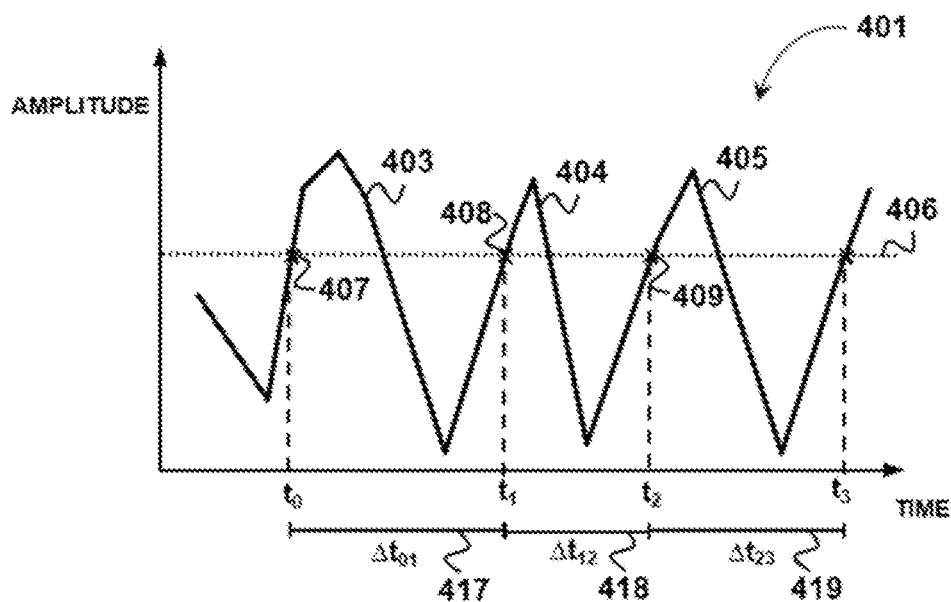
FIG. 6 schematically illustrates a graph of movement data in response to a walking activity of a user wearing a hearing device including a movement detector.

FIG. 6 illustrates an exemplary graph 401 of movement data that may be provided by movement detector 104 while the user of hearing device 100 is taking steps. The illustrated movement data can be, for instance, a y-axis component of data output by an accelerometer. As shown, the amplitude characteristic of the movement data fluctuates with a certain regularity over time. Subsequent pulses 403, 404, 405 of the movement data are produced by a respective step taken by the user. Each pulse 403-405 comprises an associated data range 407, 408, 409 at which the movement data crosses an amplitude threshold 406 from below the threshold to above the threshold. The threshold crossing points 407-409 constitute movement features representative of a walking activity of the user that can be identified by identification module 302 in the pulse sequence.

Threshold crossing points 407-409 of consecutive pulses 403-405 are separated by a respective time interval 417, 418, 419. Time intervals 417-419 can serve as a temporal characteristic of the sequence of movement features 407-409. Moreover, threshold crossing points 407-409 reoccur in the sequence over time within a certain cadence range. The cadence range may be defined by a lower limit (e.g., a particular cadence, such as 0.5 Hz) and an upper limit (e.g., a particular cadence, such as 9 Hz). The cadence range can serve as another temporal characteristic of the sequence of movement features 407-409. The temporal characteristic, for instance time intervals 417-419 and/or the cadence range, can be determined by sequence evaluation module 303. Moreover, the amplitude corresponding to threshold crossing points 407-409 and/or a peak amplitude of subsequent pulses 403-405 may be determined by sequence evaluation module 303. The amplitude characteristic may be employed as another information characteristic for the sequence of movement features 407-409. In particular, the amplitude characteristic may be correlated with a respective temporal characteristic, for instance time intervals 417-419. This can allow an identification of the sequence of movement features associated with a particular walking behavior of the user.

Data record 309 maintained by record maintenance module 306 may be based on the temporal characteristic and/or the amplitude characteristic determined in such a manner at a plurality of times. The deviation measure may then be determined by deviation determination module 304 between data record 309 and the temporal characteristic and/or the amplitude characteristic determined at a later time. In this way, a walking behavior typical for the user may be identified at the later time based on the deviation measure determined below the threshold and/or a change of the walking behavior of the user may be identified at the later time based on the deviation measure determined above the threshold.

To illustrate, a user may change his walking behavior under certain circumstances and/or over time. Those circumstances can comprise a number and a difficulty of tasks performed by the user in addition to the walking activity, as wall as a cognitive capability of the user. Multiple tasks performed at the same time can increase the cognitive load as compared to a situation in which only one task is carried out such as walking or talking. When the user is involved in multiple tasks such as walking and talking and/or listening, his walking behaviour can differ from a situation in which the cognitive capability of the user is purely focused on the walking. In such a situation, the user may unconsciously compensate the increased complexity of the dual task by decreasing the difficulty of one task, for instance by walking slower when listening and/or talking. Moreover, for some people the handling of dual tasks is more difficult than for others such that the deviation between the walking behaviour with and without the additional task is rather individual. The correlation of the user's cognitive function with a number of performed tasks can also be observed in conjunction with other types of physical activities which may be represented by the movement data. The cognitive capability itself can also vary over time, for instance when the user is suffering from a cognitive decline.

Determining the deviation measure in the above described way can allow to identify such a change of the walking behavior of the user. This can be exploited for various applications. In particular, the walking activity and/or a specific type of walking activity carried out by the user may be identified based on determining whether the temporal characteristic and/or the amplitude characteristic corresponds to a predetermined parameter, in particular a predetermined set of parameters. The predetermined parameter may be fixed for a variety of users in a generic manner or individually determined for a specific user. A change of the temporal characteristic and/or the amplitude characteristic which may be provoked by a changing walking behavior of the user, however, can lead to a failure of a proper identification of the walking activity. In particular, a slower and/or unsteady walking can be harder to identify as compared to a faster walking at a steady pace. Determining the deviation measure, as described above, can be used to adjust the predetermined parameter depending on the deviation measure. Therefore, failed identifications of the user walking can be reduced or avoided. Moreover, various operations of the hearing device can be executed depending on the identified walking activity. Enhancing the reliability of the walking detection can thus also improve the functionality of those operations. As another example, determining the deviation measure can be used to determine a parameter indicative of a property of the user such as a communication behavior, a user intention, and/or a cognitive capability of the user.

Figure 7:
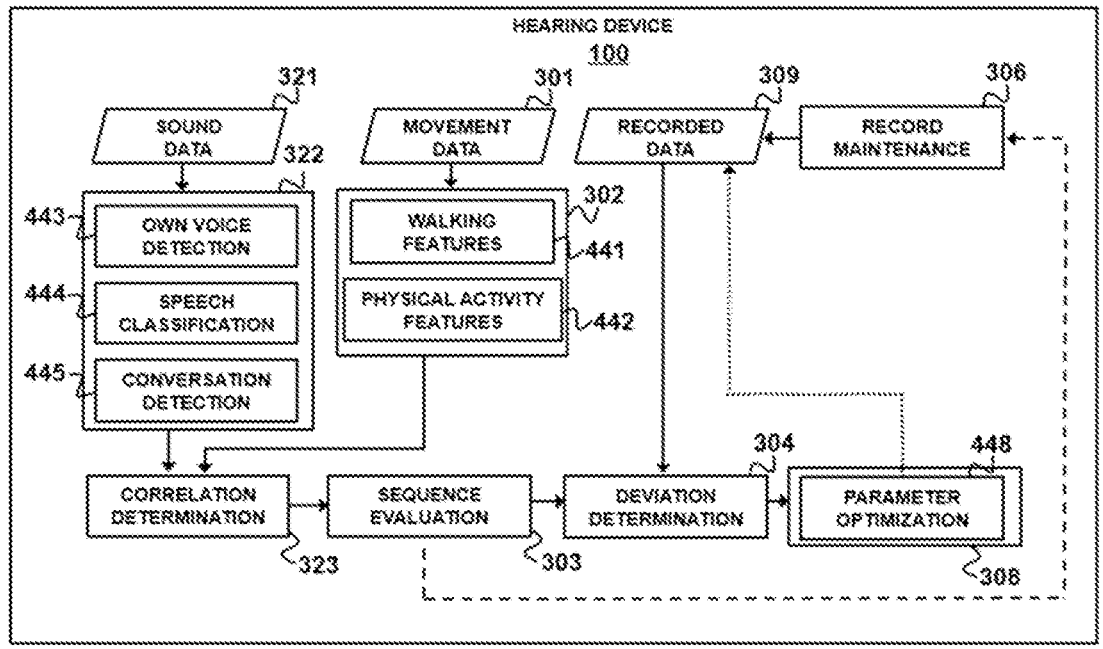
FIGS. 7-10 schematically illustrate exemplary configurations of a hearing device to identify, based on movement data, a plurality of movement features representative of a walking activity and/or another physical activity of a user in a sequence, and to determine a deviation measure of the sequence with respect to recorded data.

FIG. 7 illustrates a functional block diagram of an algorithm, which may be implemented in accordance with some implementations of the algorithm illustrated in FIG. 5. As shown, the plurality of movement features identified by feature identification module 302 in a temporal sequence can comprise features 441 representative of a walking activity of the user, as for instance movement features 407-409. The plurality of movement features can also comprise subsequent features 442 representative of another physical activity of the user. This may comprise an identification of movement features 442 recurring in a physical activity pattern of the user, analogous to the walking activity pattern described above. In some implementations, walking features 441 are identified without or independently from the identification of other physical activity features 442. In some implementations, other physical activity features 442 are identified without or independently from the identification of walking features 441. In some implementations, other physical activity features 442 are identified in addition to walking features 441 and may be correlated with each other, which may enhance the reliability of detecting a specific movement behavior of the user.

As further illustrated, feature identification module 322 may comprise an own voice detection module 443. Own voice detection module 443 can be configured to detect an own voice activity of the user based on the sound feature identified from sound data 321. Feature identification module 322 may also comprise a speech classification module 444. Speech classification module 444 can be configured to classify a speech of the user in different categories. To this end, speech classification module 444 may interact with own voice detection module 443 or may autonomously identify the user's speech before performing the classification. The classification may be performed with regard to keywords, in particular expressions and/or phrases, identified in the user's speech. The classification may also be performed with regard to speaking patterns of the user in different communication situations. For instance, a first speaking pattern may be associated with the user having a phone conversation, a second speaking pattern may be associated with the user having a direct one-to-one conversation, and a third speaking pattern may be associated with the user having a group conversation. Feature identification module 322 may also comprise a conversation detection module 444. Conversation detection module 444 can be configured to identify situations in which the user is involved in a conversation.

Correlation determination module 323 can then determine a correlation between the walking features 441 and/or other physical activity features 442 identified by movement feature identification module 302 and the user's own voice and/or classified speech and/or a detected conversation determined by sound feature identification module 322. The temporal characteristic and/or amplitude characteristic of the sequence of movement features determined by sequence evaluation module 303 can thus be associated with the user's own voice activity and/or classified speech and/or a detected conversation.

Data record 309 can then be maintained based on the temporal characteristic and/or amplitude characteristic associated with the user's own voice and/or classified speech and/or detected conversation. In particular, a plurality of data records may be maintained each associated with a different sound feature, in particular multitude of sound features. For instance, a first data record may be maintained based on the temporal characteristic and/or amplitude characteristic associated with the user's own voice. A second data record may be maintained based on the temporal characteristic and/or amplitude characteristic associated with a first category of the user's classified speech. A third data record may be maintained based on the temporal characteristic and/or amplitude characteristic associated with a second category of the user's classified speech. A fourth data record may be maintained based on the temporal characteristic and/or amplitude characteristic associated with a detected conversation.

The deviation measure determined by deviation determination module 304 can be indicative of the deviation between the data record and the temporal characteristic and/or amplitude characteristic associated with the user's own voice and/or classified speech and/or detected conversation. In particular, a plurality of data records may be employed for determining the deviation measure. In some implementations, a data record may be selected from the plurality before the deviation measure determined. The selection can be based on the user's own voice and/or classified speech and/or detected conversation associated with the temporal characteristic and/or amplitude characteristic to be compared with the data record for determining the deviation measure. In some implementations, determining the deviation measure can be carried out with respect to a plurality of data records. For instance, a first deviation measure may be determined with respect to a data record associated with the user's own voice, a second deviation measure may be determined with respect to a data record associated with a first category of the user's classified speech, a third deviation measure may be determined with respect to a data record associated with a second category of the user's classified speech, and a fourth deviation measure may be determined with respect to a data record associated with a detected conversation. The deviation measure indicating the smallest deviation to the respective data record may then be selected for further evaluation and/or processing.

The data record may comprise a first data record representative of the temporal characteristic and/or amplitude characteristic determined at a first plurality of times, wherein record maintenance module 306 is configured to control maintaining of a second data record, the second data record representative of the temporal characteristic and/or the amplitude characteristic determined at a second plurality of times, the first plurality of times temporally preceding the second plurality of times. The deviation measure determined by deviation determination module 304 can thus be indicative of a deviation between the first data record and the second data record.

As further illustrated, the operation controlled by operation control module 308 comprises a parameter optimization 448 depending on the deviation measure determined by deviation determination module 304. In some implementations, at least one parameter can be adjusted that is used to identify the walking activity and/or other physical activity carried out by the user. In particular, the parameter may be used to identify the activity associated with the user's own voice and/or classified speech and/or detected conversation. The parameter may be adjusted depending on the deviation measure, for instance corresponding to at least one temporal characteristic and/or amplitude characteristic deviating from the data record. The parameter may also be adjusted depending on the deviation between the first data record and the second data record based on the temporal characteristic and/or amplitude characteristic determined at a different plurality of times.

In some implementations, at least one parameter can be adjusted which parameter is used to perform another operation of the hearing device. The other operation can thus be performed depending on the walking activity and/or other physical activity carried out by the user, in particular when the walking activity and/or other physical activity has been determined to correlate with the user's own voice and/or classified speech and/or detected conversation. For instance, the parameter may be used for a processing of sound data. In particular, the parameter may be an optimized parameter for controlling a property of an acoustic beam formed by hearing device 100.

Parameter optimization module 448 may be configured to maintain a record of the adjusted parameter in a memory, as illustrated by a dotted arrow, such that it can be accessed at a later time. The optimized parameter may be recorded depending on the temporal characteristic and/or amplitude characteristic determined by sequence evaluation module 303. The optimized parameter may further be recorded depending on the user's own voice and/or classified speech and/or detected conversation associated with the temporal characteristic and/or amplitude characteristic.

Figure 8:
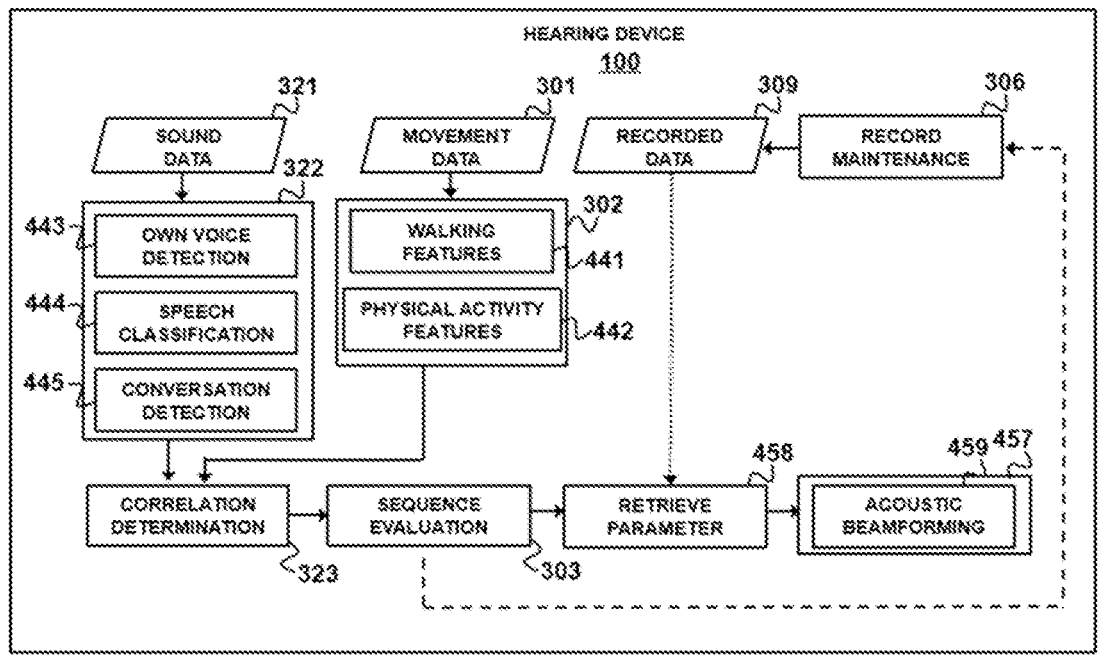

FIG. 8 illustrates a functional block diagram of an algorithm for controlling a property of an acoustic beam based on movement data and sound data that may be executed by processor 102. The algorithm comprises modules 302, 303, 306, 322, 323 described above. The algorithm may be executed after the algorithm illustrated in FIG. 7 has been performed.

As shown, the temporal characteristic and/or amplitude characteristic determined by sequence evaluation module 303 is input to a parameter retrieving module 458. Parameter retrieving module 458 is configured to retrieve the optimized parameter adjusted by parameter optimization module 448, as used in the algorithm illustrated in FIG. 7. For instance, as illustrated by a dotted arrow, the optimized parameter may be retrieved from recorded data 309. The retrieved optimized parameter may depend on the temporal characteristic and/or amplitude characteristic determined by sequence evaluation module 303. The retrieved optimized parameter may further be depend on the user's own voice and/or classified speech and/or detected conversation associated with the temporal characteristic and/or amplitude characteristic.

The retrieved parameter can then be used, in a operation control module 457, to identify the walking activity and/or other physical activity carried out by the user, in particular a walking activity and/or other physical activity which is typical during an occurrence of the user's own voice and/or classified speech and/or detected conversation. The retrieved parameter may comprise, for instance, an allowed value range and/or a threshold of the temporal characteristic and/or amplitude characteristic determined by sequence evaluation module 303 such that it allows to draw a conclusion that the walking activity and/or other physical activity is carried out by the user.

To illustrate, the user may walk slower and/or at a more irregular pace when he is involved in a conversation. Such a walking activity can be, per se, more difficult to detect, even more so when the detection is solely based on the temporal characteristic and/or amplitude characteristic of the sequence of movement features. Retrieving the optimized parameter which is associated with the user's own voice and/or classified speech and/or detected conversation typically occurring during such a conversation, however, can allow to apply the optimized parameter more efficiently for identifying the walking activity.

The retrieved parameter can also be used, in operation control module 457, to perform another operation of the hearing device. In the illustrated example, the retrieved parameter is input to an acoustic beamforming algorithm 459. The retrieved parameter can thus be used to control a property of the acoustic beam. Controlling the property may comprise reducing a directivity of the acoustic beam, in particular enlarging a width of the acoustic beam, or increasing a directivity of the acoustic beam, in particular reducing a width of the acoustic beam, and/or changing a spatial direction of the acoustic beam. The retrieved parameter can also be employed to activate and/or deactivate acoustic beamforming algorithm 459.

To illustrate, the user may walk in a noisy environment and have a conversation with a person walking next to him. In such a situation, a common hearing device controller may detect a "speech in noise" program and automatically activate the beamforming algorithm with a high directivity. This could suppress the voice of the speaker on the side of the user. Such an undesired operation could be corrected by always reducing the beamforming directivity when a walking activity of the user is detected. But detecting the walking activity in a usual way may be difficult when the user is involved in a conversation for the above mentioned reasons that the walking behavior of the user may change in such a situation. Retrieving the optimized parameter which is associated with the user's own voice and/or classified speech and/or detected conversation typically occurring during such a conversation, however, can allow to control the beamforming more accurately matched with the user's needs.

Figure 9:
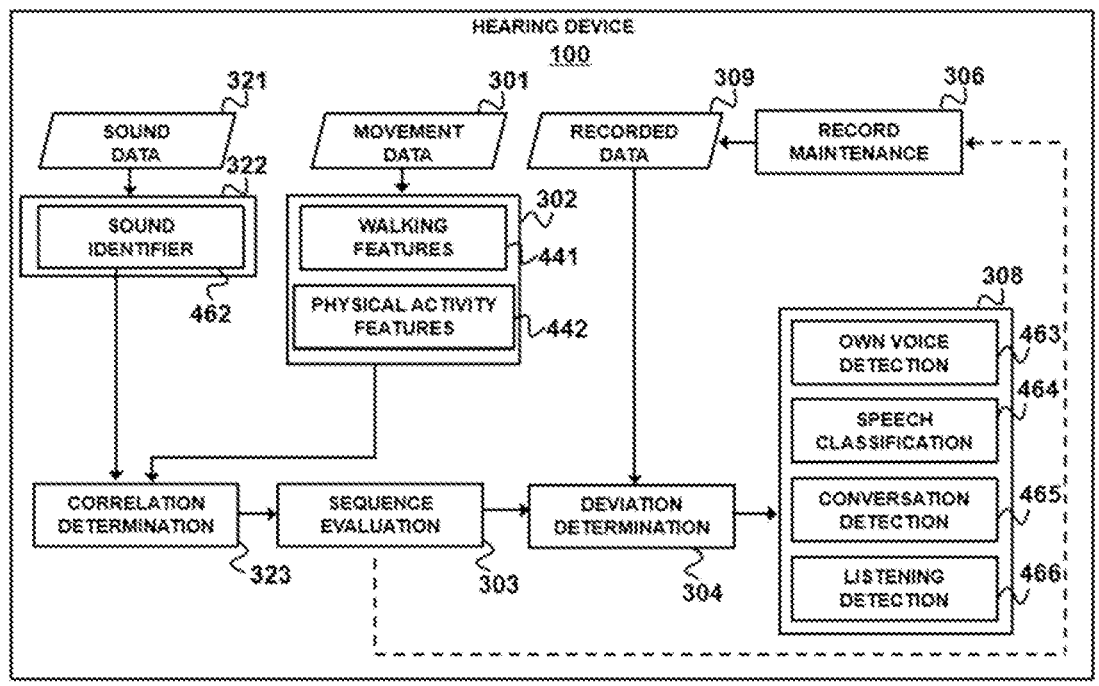

FIG. 9 illustrates a functional block diagram of an algorithm for detecting a speech characteristic of the user based on movement data and sound data that may be executed by processor 102. The algorithm comprises modules 302-306, 322, 323 described above. The algorithm may be executed after the algorithm illustrated in FIG. 5 and/or in FIG. 7 has been performed.

As shown, sound feature identification module 322 comprises a sound identifier 462 configured to determine the occurrence of a sound based on sound data 321. Sound data 321 may include data representative of a speech of the user and/or data representative of other sound unrelated to a speech of the user. For instance, sound data 321 may be provided by a rather basic sound detector such as a single-channel microphone. Sound identifier 462 may thus be configured to identify the sound feature in a rather quick and uncomplicated way. The sound feature identified by sound identifier 462 may be indicative for the occurrence of any sound, for instance a sound exceeding a certain signal-to-noise ration (SNR) and/or a sound within a certain frequency range. In some instances, the sound feature identified by sound identifier 462 may also comprise indications of a speech activity of the user which may be used to identify the speech activity with a certain uncertainty. In some instances, the identified sound feature does not allow to distinguish between a speech of the user, such as the user's own voice and/or classified speech and/or a detected conversation, and ambient sound generated by other sound sources in the environment of the user.

After determining, by correlation determination module 323, a correlation between the sound identified by sound identifier 462 and the walking features 441 and/or other physical activity features 442 identified by movement feature identification module 302, the temporal characteristic and/or amplitude characteristic of the sequence of walking features 441 and/or other physical activity features 442 is determined by sequence evaluation module 303 and input to deviation determination module 304. Deviation determination module 304 can determine the deviation measure indicative of a deviation between data record 309 and the temporal characteristic and/or amplitude characteristic input from sequence evaluation module 303. As described above in conjunction with FIG. 7, data record 309 can comprise a plurality of data records each associated with a different property of the user's speech. For instance, a first data record may be associated with the user's own voice, a second data record associated with a first category of the user's classified speech, a third data record associated with a second category of the user's classified speech, and/or a fourth data associated with a detected conversation.

Operation control module 308 comprises at least one of an own voice detection module 463, a speech classification module 464, a conversation detection module 465, and a listening intention detection module 466. Own voice detection module 463 can be configured to determine a parameter indicative of an own voice activity of the user depending on the deviation measure, in particular when the deviation measure is below a threshold. Speech classification module 464 can be configured to determine a parameter indicative of a category of a speech of the user depending on the deviation measure, in particular when the deviation measure is below a threshold. Conversation detection module 465 can be configured to determine a parameter indicative of situations in which the user is involved in a conversation depending on the deviation measure, in particular when the deviation measure is below a threshold. Listening intention detection module 466 can be configured to determine a parameter indicative of situations in which the user has a listening intention depending on the deviation measure, in particular when the deviation measure is below a threshold. For instance, a listening intention may be derived from situations in which the user is involved in a conversation and shows a specific walking behavior during speaking in the conversation. The listening intention may then be determined at a later time based on a comparison with the temporal characteristic and/or amplitude characteristic determined earlier during the conversation, even when the user is not actively participating in a conversation at the later time but shows a corresponding walking and/or other movement behavior.

In this way, operation control module 308 can be configured to detect a speech situation involving the user's own voice and/or a speech category and/or a conversation and/or a listening intention. Operation control module 308 may also be configured to provide complementary evidence for a presence of such a speech situation in addition to other evidence which may be determined with a given uncertainty. Operation control module 308 can be further configured to control a hearing device operation optimized for the speech situation. For instance, a signal processing of sound data may be controlled depending of the speech situation. Operation control module 308 may be further configured to provide a notification based on the parameter indicative of the own voice activity and/or listening intention and/or speech classification and/or conversation situation. The notification may be output to the user via a user interface. The notification may propose, for instance, a hearing device operation to the user which may be optimized for the identified speech situation such that the user is enabled to select the optimized operation.

Figure 10:
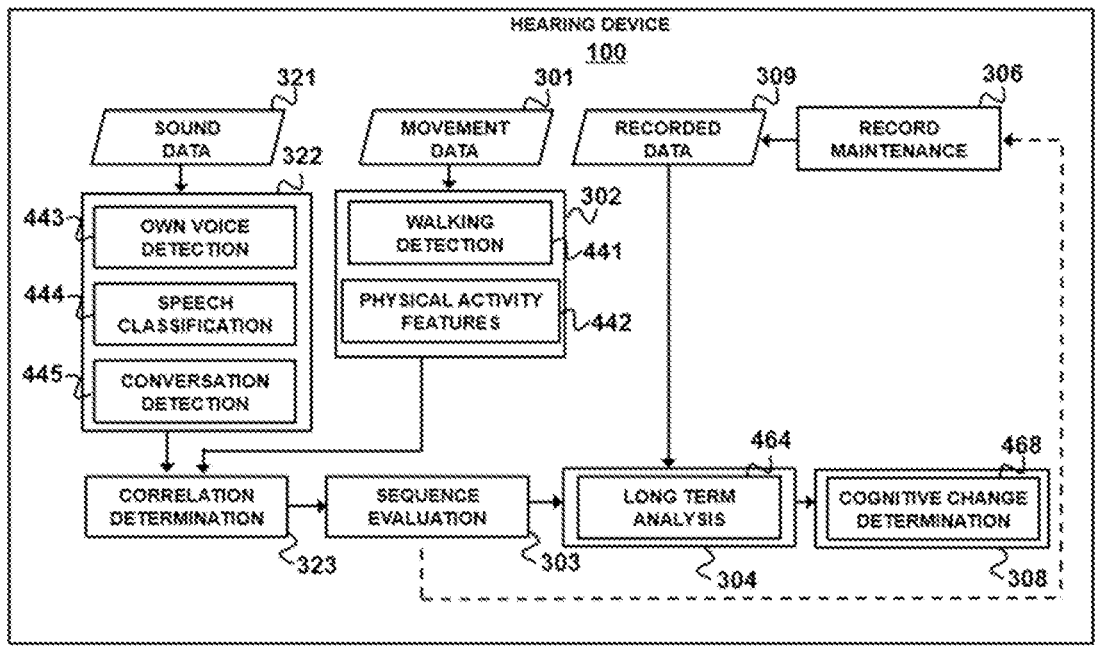

FIG. 10 illustrates a functional block diagram of an algorithm, which may be implemented in accordance with some implementations of the algorithm illustrated in FIG. 5 and/or in FIG. 7. The algorithm comprises modules 302-306, 322, 323 described above. As shown, deviation determination module 304 comprises a long term analysis module 464. Long term analysis module 464 is configured to determine the deviation measure such that the deviation measure is representative of a deviation between the temporal characteristic and/or amplitude characteristic determined at a first plurality of times, in particular over a first period, and the temporal characteristic and/or amplitude characteristic determined at a second plurality of times, in particular over a second period. The first period may be temporally preceding the second period. Each of the first period and second period may correspond to a long term, for instance a plurality of times per day during the course of several days or weeks or months or years.

To this end, a first data record may be maintained by record maintenance module 306 based on the temporal characteristic and/or the amplitude characteristic determined at the first plurality of times, and a second data record may be maintained by record maintenance module 306 based on the temporal characteristic and/or the amplitude characteristic determined at the second plurality of times. The deviation measure determined by long term analysis module 464 can thus be indicative of a deviation between the first data record and the second data record. The deviation measure may be based on a statistical measure of the temporal characteristic and/or the amplitude characteristic in the first data record and/or in the second data record. The statistical measure may comprise, for instance, a mean value and/or a variance and/or a standard deviation.

As further illustrated, operation control module 308 comprises a cognitive change determination module 468. Cognitive change determination module 468 is configured to determine a parameter indicative of a change of a cognitive capability of the user depending on the deviation measure. In particular, the parameter may be indicative of a cognitive decline of the user when the deviation measure is indicative of a temporal characteristic indicating a longer time interval between movement features 407-409 as compared to earlier times in which the temporal characteristic of movement features 407-409 has been determined. Alternatively or additionally, the parameter may be indicative of a cognitive decline of the user when the deviation measure is indicative of a deviation between the amplitude characteristic determined in the sequence of movement features 407-409. For instance, a more irregular amplitude pattern of the subsequent movement features may serve as an indication of a cognitive change.

To illustrate, the dual task of having a conversation during walking depends on the cognitive capability of the user and can be even harder to accomplish when the user is suffering from a cognitive decline as compared to earlier situations of a steady cognitive capability. The user may compensate the increased difficulty by altering his walking behaviour, in particular by walking slower and/or less regular. The deviation measure can indicate such a change of the walking behaviour and therefore may be used as an indicator for an onset of an cognitive decline.

Operation control module 308 may be further configured to provide a notification based on the parameter indicative of the change of the cognitive capability, in particular information about the indications of a cognitive decline. Providing the notification may comprise, for instance, informing the user via a voice message about a potential risk and recommend to see a doctor, e.g. a general practitioner, and/or informing the user via a smartphone message about a potential risk and provide specific information about possible medical contacts in the area and/or transmitting the information to a remote device, in particular to a remote medical service, e.g. a registered general practitioner or a dedicated specialist, to let him assess the information and follow up with the user. In addition, an alarm flag may be raised in a control program of the hearing device such that other operations of the hearing device may be performed in consideration of a possible cognitive decline of the user.

Figure 11:
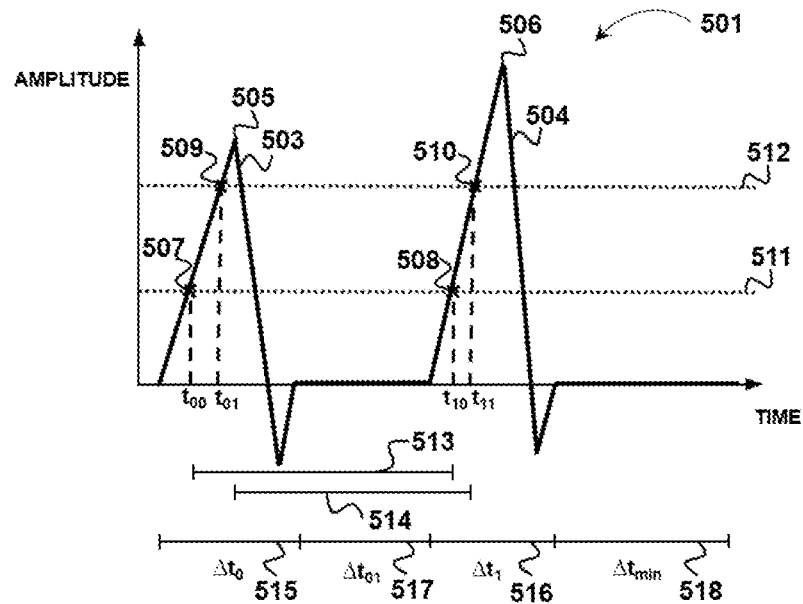
FIG. 11 schematically illustrates a graph of movement data in response to a tapping activity of a user wearing a hearing device including a movement detector.

FIG. 11 illustrates an exemplary graph 501 of movement data that may be provided by movement detector 104 while the user of hearing device 100 is performing sequential manual tappings causing a movement of a housing of hearing device 100. The illustrated movement data can be, for instance, a single axis component of a three-dimensional data output by an accelerometer. The graph 501 shows two signal pulses 503, 504 over time produced by two taps, a first tap 503 followed by a second tap 504.

First tap 503 has a peak in amplitude at 505, and second tap has a peak in amplitude at 506. First tap 503 has measurable movement effects that last for a duration period 515 and second tap 504 has measurable effects that last for duration period 516. Each pulse 503, 504 has a positive slope until peak 505, 506. After the peak 505, 506, there is a shock period that relates to the acceleration of the hearing device in response to the tap. During the shock period, each pulse 503, 504 has a negative slope, which indicates movement in the opposite direction. As shown, the slope may change sign several times during the shock period. The positive slope before peaks 505, 506 can be employed as movement features representative of a tapping activity of the user that can be identified by identification module 302 in the pulse sequence. For example, identification module 302 may only register a tap if the respective slope is above a slope threshold. The slope may be identified by determining a time interval between a first data range 507, 508 at which the movement data crosses a first amplitude threshold 511 from below the threshold to above the threshold, and a second data range 509, 510 at which the movement data crosses a second amplitude threshold 512 larger than first amplitude threshold 511 from below the threshold to above the threshold.

Additionally shown, there is a quiet period 517 between the first tap and the second tap, which refers to when little to no changes in movement are detected. Depending on a person's double tapping pattern, the quiet period 517 (or another quiet period after the second tap) can vary. Quiet period 517 can be used as a temporal characteristic of the sequence of movement features 507-510. A double tapping activity of the user may be distinguished from a single tapping and/or a triple tapping depending on quiet period 517 not exceeding a maximum period 518. The number of identified movement features 507-510 separated by a time interval smaller then maximum period 518 can be used as another temporal characteristic. A time interval 513 between first threshold crossing points 507, 508 and/or a time interval 514 between second threshold crossing points 509, 510 can be used as another temporal characteristic. The temporal characteristic can be determined by sequence evaluation module 303. In addition, the amplitude corresponding to threshold crossing points 507-510 and/or peak amplitude 505, 506 of subsequent pulses 503-504 may be determined by sequence evaluation module 303. The amplitude may be employed as another information characteristic for the sequence of movement features. In particular, the amplitude characteristic may be correlated with a respective temporal characteristic.

Figure 12:
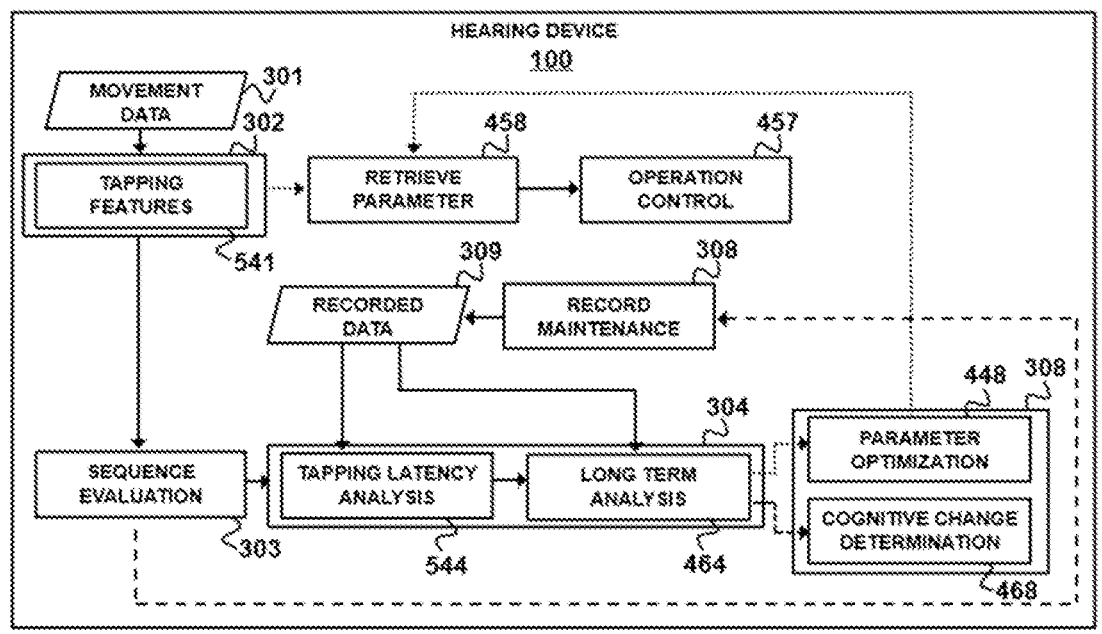
FIG. 12 schematically illustrates an exemplary configuration of a hearing device to identify, based on movement data, a plurality of movement features representative of a tapping activity of a user in a sequence, and to determine a deviation measure of the sequence with respect to recorded data.

FIG. 12 illustrates a functional block diagram of an algorithm, which may be implemented in accordance with some implementations of the algorithm illustrated in FIG. 3. As shown, the movement features identified by feature identification module 302 comprise features 541 representative of a tapping activity of the user, as for instance movement features 507-510. Deviation determination module 304 comprises a tapping latency analysis module 544. Tapping latency analysis module 544 is configured to determine the deviation measure representative of a latency between subsequent taps 503, 504 as compared to the temporal characteristic of subsequent taps 503, 504 recorded in data record 306. Deviation determination module 304 further comprises long term analysis module 464, as described in conjunction with FIG. 10. In this way, a long term deviation of the tapping latency at a later time period may be determined relative to an earlier time period.

Operation control module 308 may comprise cognitive change determination module 468, as described in conjunction with FIG. 10, configured to determine a parameter indicative of a change of a cognitive capability of the user depending on the deviation measure. To illustrate, the task of performing multiple tappings at a row can depend on the cognitive capability of the user. When the user is suffering from a cognitive decline, the user may perform the sequence of tappings in a more irregular fashion and/or at a slower tapping rate, at least when averaged over time. The deviation measure, in particular a slowed down temporal characteristic and/or a more irregular amplitude pattern, can indicate such a change of the tapping behaviour and therefore may be used as an indicator for a cognitive decline. Operation control module 308 may be further configured to provide a notification based on the parameter indicative of the change of the cognitive capability, as described above.

Operation control module 308 may comprise parameter optimization module 448, as described in conjunction with FIG. 7, configured to optimize a parameter of a hearing device operation depending on the deviation measure determined by deviation determination module 304. The optimized parameter can be retrieved by parameter retrieving module 458, as described in conjunction with FIG. 8. In particular, operation control module 457 may be configured to control a hearing device operation depending on tapping features 541 identified by feature identification module 302 and/or the temporal characteristic and/or amplitude characteristic determined by sequence evaluation module 303. Such an operation may comprise, for example, detecting a tapping activity of the user, in particular a certain type of tapping, and/or adjusting a volume and/or switching and/or modifying a hearing device program and/or accepting/rejecting a phone call. Before the operation is controlled by operation control module 457, the optimized parameter for performing the operation can be retrieved by parameter retrieving module 458 and input to operation control module 457. To this end, the optimized parameter may be stored in data record 309 by parameter optimization module 448 and may be retrieved by parameter retrieving module 458 from data record 309 at a later time.

Figure 13:
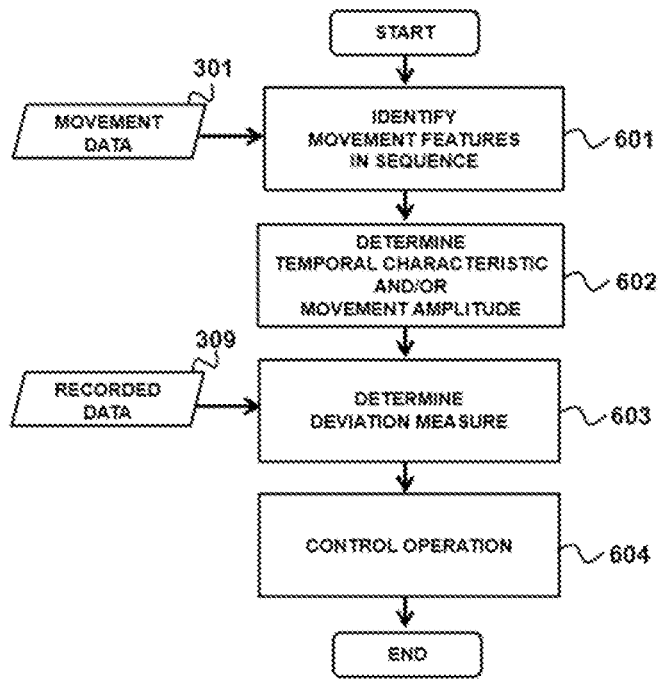
FIGS. 13-19 illustrate exemplary methods of operating a hearing device according to principles described herein.

FIG. 13 illustrates a block flow diagram for a method of operating a hearing device. The method may be executed by processor 102, in particular by executing the data processing algorithm illustrated in any of FIGS. 3-5, 7-10, and 12. At 601, a plurality of movement features is identified in a sequence based on movement data 301. At 602, a temporal characteristic of the sequence of movement features is determined and/or an amplitude characteristic of the movement data associated with at least one of the movement features identified in the sequence is determined. At 603, a deviation measure indicative of a deviation between data record 309 and the temporal characteristic and/or the amplitude characteristic is determined. At 604, an operation of the hearing device is controlled depending on the deviation measure.

Figure 14:
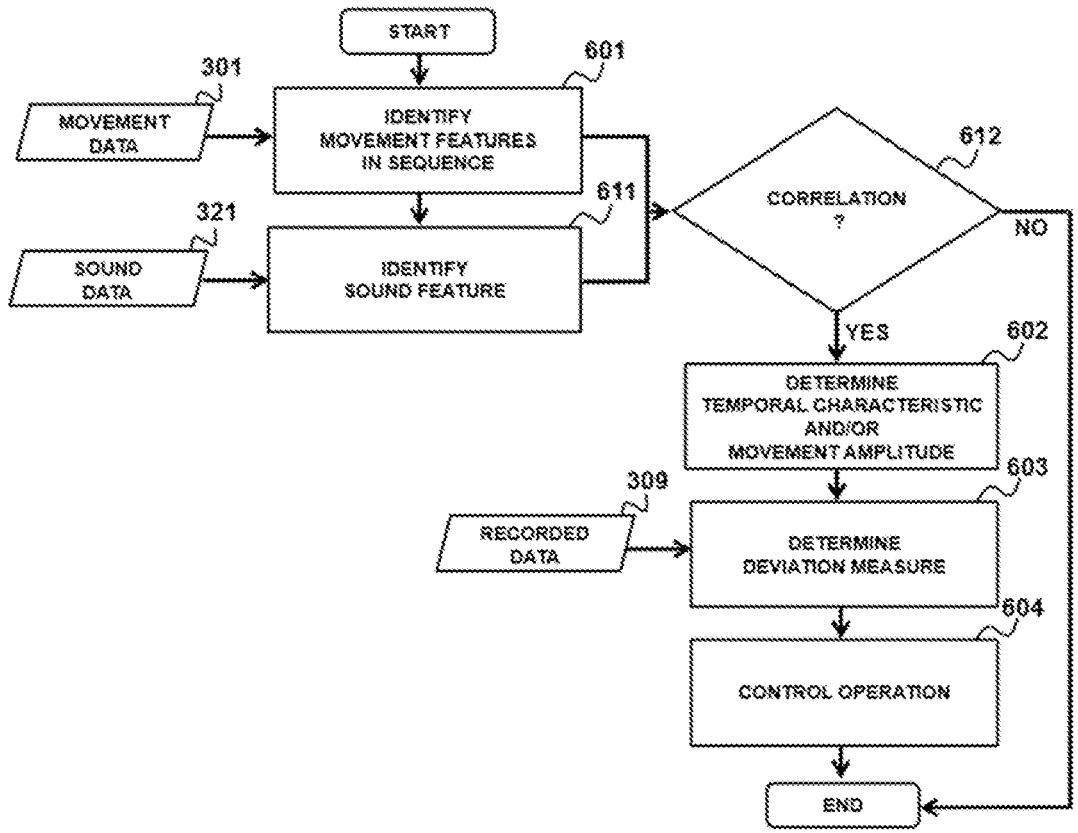

FIG. 14 illustrates another block flow diagram for a method of operating a hearing device. The method may be executed by processor 102, in particular by executing the data processing algorithm illustrated in any of FIGS. 5, and 7-10. At 611, a sound feature is identified from sound data 321. At 612, a temporal correlation between the sound feature and the sequence of movement features is determined. Depending on the correlation, in particular when a degree of correlation exceeds a threshold, the temporal characteristic and/or the amplitude characteristic of the sequence of movement features is determined at 602. In this way, the temporal characteristic and/or the amplitude characteristic is associated with the sound feature. Determining the deviation measure can thus be executed at 603 between the temporal characteristic and/or the amplitude characteristic associated with the sound feature and data record 309.

Figure 15:
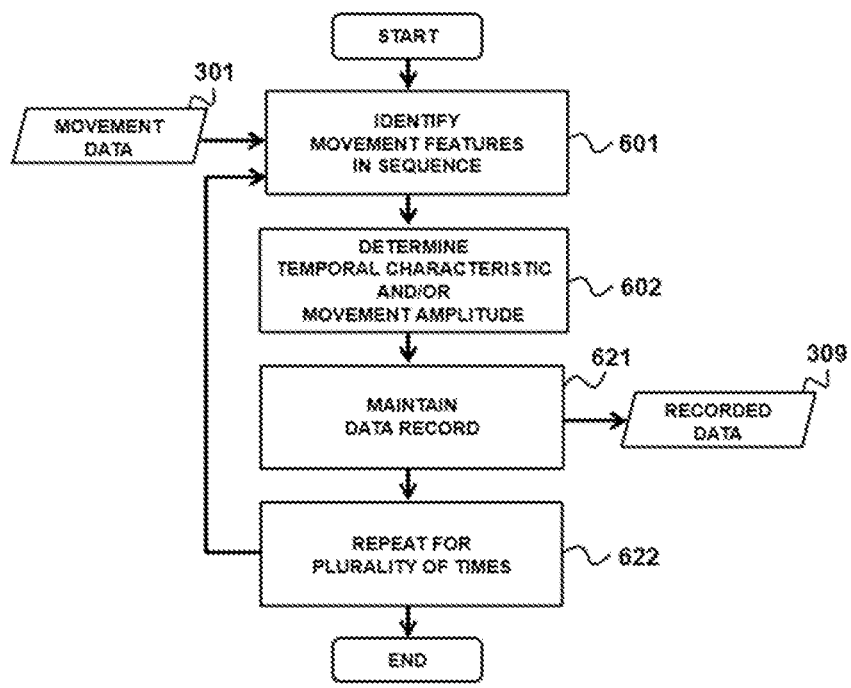

FIG. 15 illustrates another block flow diagram for a method of operating a hearing device. The method may be executed by processor 102, in particular by executing the data processing algorithm illustrated in any of FIGS. 3-5, 7-10, and 12. The method may be employed to provide data record 309. After identifying the movement features at 601 and determining the temporal characteristic and/or amplitude characteristic at 602 for a first time, data record 309 is maintained based on the determined temporal characteristic and/or amplitude characteristic. This may comprise storing a value representative of the determined temporal characteristic and/or amplitude characteristic in data record 309. At 622, steps 601, 602, 621 are repeated for a plurality of times, wherein maintaining data record 309 at 621 comprises updating data record 309, for instance by data logging, based on the temporal characteristic and/or amplitude characteristic determined at 602 at the respective time. Step 622 may comprise repeating steps 601, 602, 621 over a long term. Step 621 may comprise including a statistical measure of the temporal characteristic and/or amplitude characteristic in data record 309.

Figure 16:
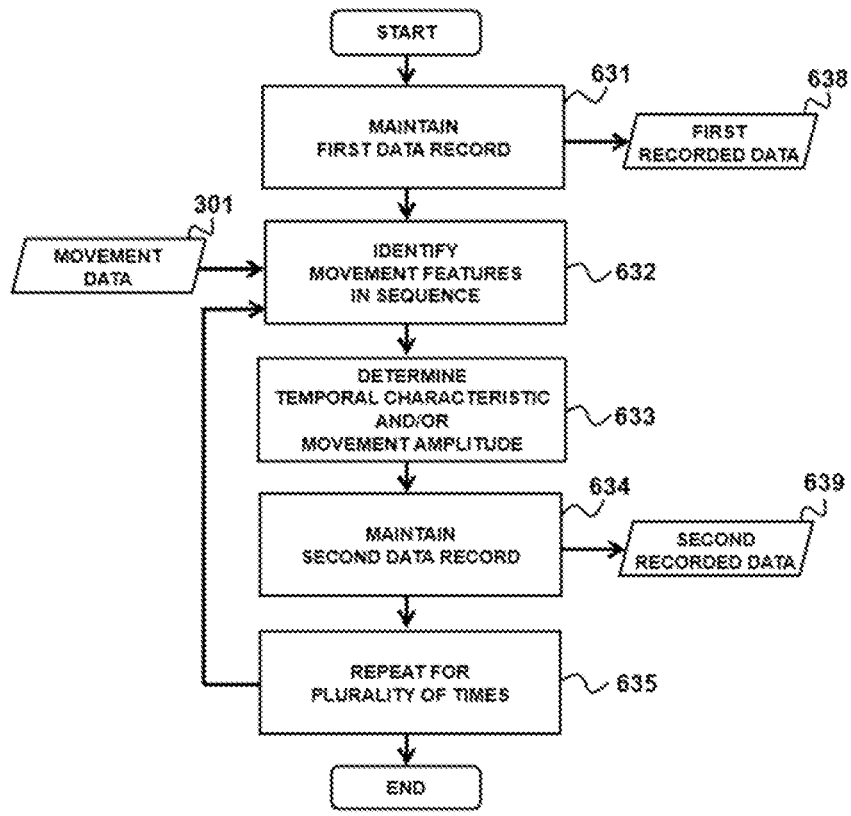

FIG. 16 illustrates another block flow diagram for a method of operating a hearing device. The method may be executed by processor 102, in particular by executing the data processing algorithm illustrated in any of FIGS. 3-5, 7-10, and 12. The method may be employed to provide a first data record 638 and a second data record 639. In particular, the method may be implemented by employing long term analysis module 464 illustrated in FIGS. 10 and 12. Data record 309 may comprise first data record 638. At 631, a maintaining of first data record 638 may be performed in accordance with step 621 in the method illustrated in FIG. 15. Steps 601, 602, and 622 may be correspondingly applied. First data record 638 can thus be based on the temporal characteristic and/or the amplitude characteristic determined at a first plurality of times. Second data record 639 can be based on the temporal characteristic and/or the amplitude characteristic determined at a second plurality of times temporally succeeding the first plurality of times. To this end, identifying the movement features based on movement data 301 provided at the temporally succeeding times can be performed at 632 and determining the temporal characteristic and/or amplitude characteristic can be performed at 633 based on which second data record 639 is maintained at 634. At 635, steps 632, 633, 634 are repeated for the second plurality of times, in particular over a long term. Step 634 may also comprise including a statistical measure of the temporal characteristic and/or amplitude characteristic in data record 309.

Figure 17:
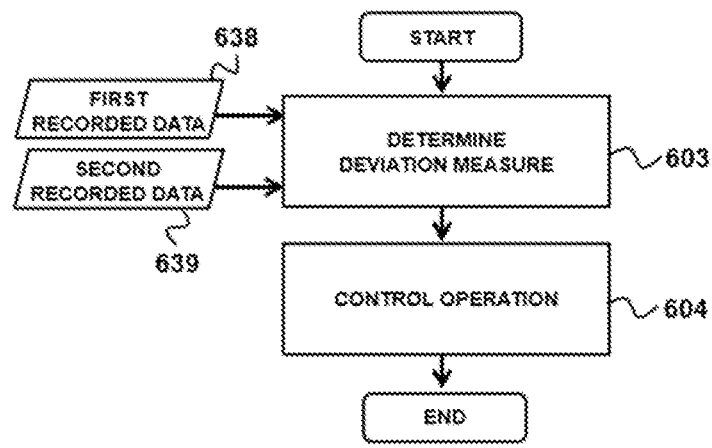

FIG. 17 illustrates another block flow diagram for a method of operating a hearing device. The method may be executed by processor 102, in particular by executing the data processing algorithm illustrated in any of FIGS. 3-5, 7-10, and 12. The method may be executed after the method illustrated in FIG. 16 has been performed. The deviation measure is determined at 603 based on first data record 638 and second data record 639 such that it is indicative of a deviation between first data record 638 and second data record 639. Depending on the deviation measure, the operation of the hearing device is controlled at 604.

Figure 18:
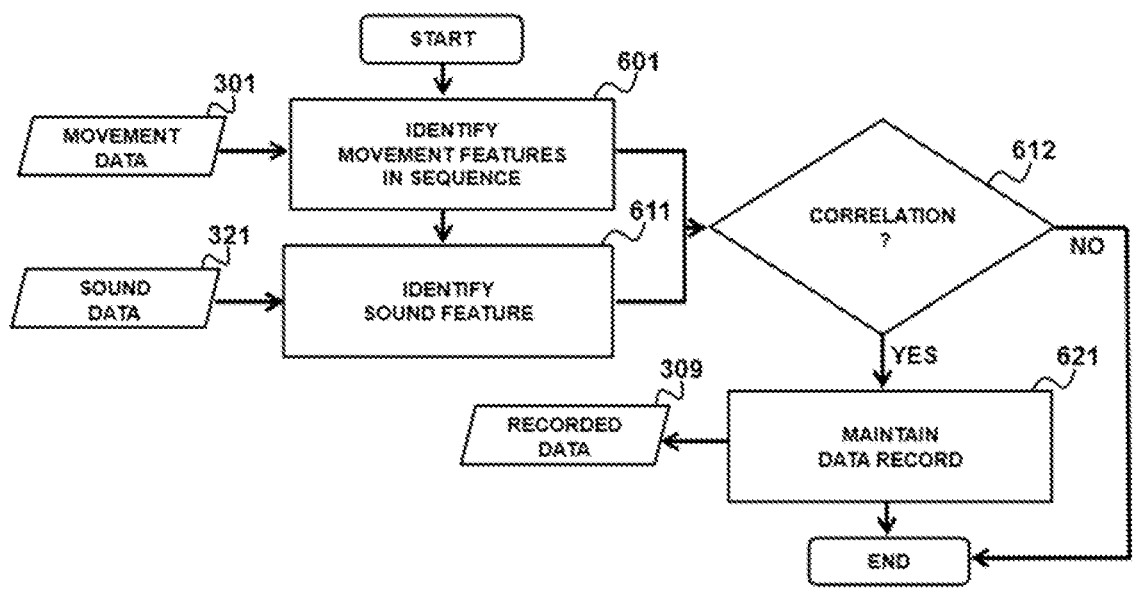

FIG. 18 illustrates another block flow diagram for a method of operating a hearing device. The method may be executed by processor 102, in particular by executing the data processing algorithm illustrated in any of FIGS. 5, and 7-10. The method may be employed to provide data record 309. After identifying the movement features from movement data 301 at 601, determining the sound feature from sound data 321 at 611, and determining the temporal correlation at 612, data record 309 is maintained at 621 depending on the correlation. In this way, the temporal characteristic and/or the amplitude characteristic based on which data record 309 is maintained is associated with the sound feature.

Figure 19:
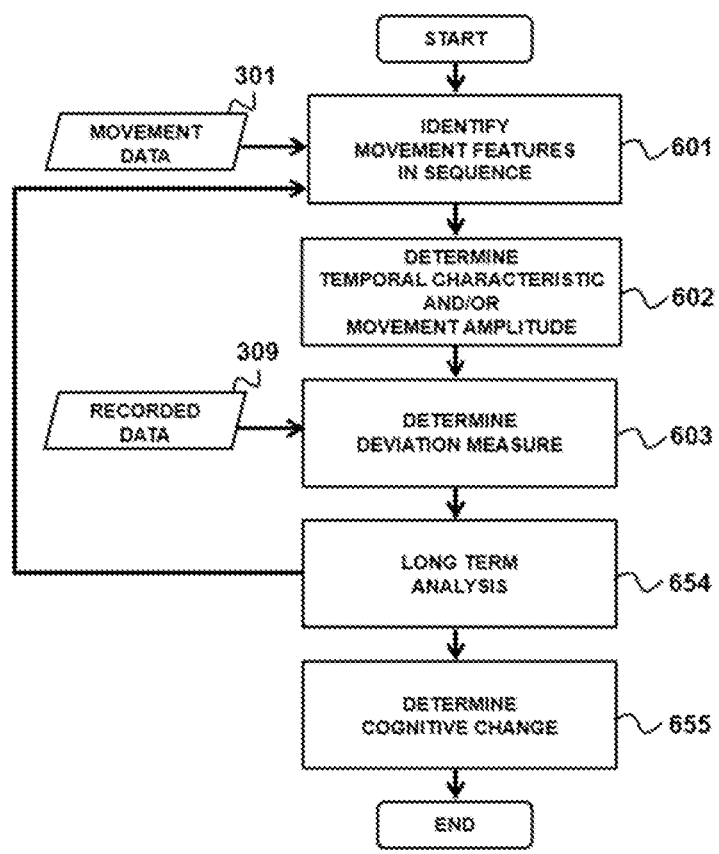

FIG. 19 illustrates another block flow diagram for a method of operating a hearing device. The method may be executed by processor 102, in particular by executing the data processing algorithm illustrated in any of FIGS. 3-5, 7-10, and 12. At 654, a long term analysis of the deviation measure determined at 603 is performed. This may comprise the operations of the method illustrated in FIG. 16. At 655, parameter indicative of a change of a cognitive capability of the user is determined depending on the deviation measure. Subsequently, a notification based on the parameter may be provided.

While the principles of the disclosure have been described above in connection with specific devices and methods, it is to be clearly understood that this description is made only by way of example and not as limitation on the scope of the invention. The above described preferred embodiments are intended to illustrate the principles of the invention, but not to limit the scope of the invention. Various other embodiments and modifications to those preferred embodiments may be made by those skilled in the art without departing from the scope of the present invention that is solely defined by the claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A hearing device comprising
a housing configured to be worn at an ear of a user;
a movement detector mechanically coupled to the housing, the movement detector configured to provide movement data indicative of a movement of the housing; and
a processor communicatively coupled to the movement detector, the processor configured to identify, based on the movement data, a plurality of movement features in a sequence, the movement features representative of a movement activity carried out by the user, and to determine a temporal characteristic of the sequence of movement features and/or to determine an amplitude characteristic of the movement data associated with at least one of the movement features identified in the sequence;
characterized in that the processor is further configured to
control maintaining of a data record representative of the temporal characteristic and/or the amplitude characteristic determined at a plurality of times; to
determine a deviation measure indicative of a deviation between the data record and the temporal characteristic and/or the amplitude characteristic determined at a time later than said plurality of times; and to
control an operation of the hearing device depending on the deviation measure.

2. The device according to claim 1, characterized in that the hearing device comprises a sound detector configured to provide sound data indicative of a detected sound, the processor communicatively coupled to the sound detector and configured to
identify a sound feature from the sound data; and to associate said temporal characteristic and/or said amplitude characteristic with the sound feature depending on a temporal correlation between the sound feature and the sequence of movement features.

3. The device according to claim 2, characterized in that the sound detector comprises a microphone and/or a voice activity detector (VAD).

4. The device according to claim 2, characterized in that the sound feature is representative of an own voice activity of the user.

5. The device according to claim 1, characterized in that the movement features are representative of a walking activity of the user.

6. The device according to claim 1, characterized in that the movement features are representative of sequential manual tappings causing the movement of the housing.

7. The device according to claim 1, characterized in that the processor is configured to identify the movement activity carried out by the user based on determining whether the temporal characteristic and/or the amplitude characteristic corresponds to a predetermined parameter.

8. The device according to claim 7, characterized in that the operation comprises adjusting the predetermined parameter depending on the deviation measure.

9. The device according to claim 1, characterized in that the operation comprises determining a parameter indicative of a listening intention of the user and/or a parameter indicative of an own voice activity of the user and/or a parameter indicative of a change of a cognitive capability of the user depending on the deviation measure.

10. The device according to claim 9, characterized in that the parameter is indicative of a cognitive decline of the user when the deviation measure determined at said plurality of times is indicative of a shorter time interval between the movement features as compared to the time interval determined at the time later than said plurality of times.

11. The device according to claim 1, characterized in that the hearing device comprises a microphone configured to detect ambient sound and a beamformer configured to form an acoustic beam based on the detected sound, wherein the operation comprises determining an optimized parameter for controlling a property of the acoustic beam.

12. The device according to claim 1, characterized in that the operation comprises providing a notification depending on the deviation measure.

13. The device according to claim 1, characterized in that the data record is a first data record representative of the temporal characteristic and/or the amplitude characteristic determined at a first plurality of times, the processor configured to control maintaining of a second data record, the second data record representative of the temporal characteristic and/or the amplitude characteristic determined at a second plurality of times, the first plurality of times temporally preceding the second plurality of times, wherein the deviation measure is indicative of a deviation between the first data record and the second data record.

14. The device according to claim 1, characterized in that the data record comprises a statistical measure of the temporal characteristic and/or the amplitude characteristic determined at said plurality of times.

15. A method of operating a hearing device comprising a housing configured to be worn at an ear of a user, the method comprising
providing movement data indicative of a movement of the;
identifying, based on the movement data, a plurality of movement features in a sequence, the movement features representative of a movement activity carried out by the user; and
determining a temporal characteristic of the sequence of movement features and/or determining an amplitude of the movement data associated with at least one of the movement features identified in the sequence,
characterized by
maintaining a data record representative of the temporal characteristic and/or the amplitude characteristic determined at a plurality of times;
determining a deviation measure indicative of a deviation between the data record and the temporal characteristic and/or the amplitude characteristic determined at a time later than said plurality of times; and
controlling an operation of the hearing device depending on the deviation measure.

* * * * *